(12) United States Patent
Matsuzaki et al.

(10) Patent No.: US 7,244,569 B2
(45) Date of Patent: Jul. 17, 2007

(54) PLASMID AUTONOMOUSLY REPLICABLE IN CORYNEFORM BACTERIA

(75) Inventors: Yumi Matsuzaki, Kawasaki (JP); Eiichiro Kimura, Kawasaki (JP); Tsuyoshi Nakamatsu, Kawasaki (JP); Osamu Kurahashi, Kawasaki (JP); Yoshio Kawahara, Kawasaki (JP); Shinichi Sugimoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 334 days.

(21) Appl. No.: 10/832,299

(22) Filed: Apr. 27, 2004

(65) Prior Publication Data

US 2004/0197918 A1 Oct. 7, 2004

Related U.S. Application Data

(62) Division of application No. 09/636,458, filed on Aug. 11, 2000, now Pat. No. 6,905,819.

(30) Foreign Application Priority Data

Aug. 12, 1999 (JP) ................................. 11-228391

(51) Int. Cl.
C12N 15/74 (2006.01)
C12N 15/77 (2006.01)
C12N 15/10 (2006.01)
C12N 15/31 (2006.01)
C07H 21/04 (2006.01)
C07K 14/195 (2006.01)
C07K 14/34 (2006.01)

(52) U.S. Cl. ........................ 435/6; 435/320.1; 435/243; 435/252.1; 536/23.1; 536/23.2; 536/23.7

(58) Field of Classification Search ...................... None
See application file for complete search history.

(56) References Cited

U.S. PATENT DOCUMENTS 4,617,267 A 10/1986 Katsumata et al. ............ 435/91
5,250,434 A 10/1993 Yamada et al. ............ 435/252.1
6,461,852 B1 10/2002 Tsujimoto et al.
2002/0155556 A1 10/2002 Imaizumi et al.
2002/0160461 A1 10/2002 Nakai et al.
2003/0013174 A1 1/2003 Tsujimoto et al.
2003/0049805 A1 3/2003 Nagase et al.
2003/0054506 A1 3/2003 Otsuna et al.
2003/0166174 A1 9/2003 Ono et al.
2003/0232338 A1 12/2003 Usuda et al.
2004/0121428 A1 6/2004 Sugimoto et al.
2004/0170985 A1 9/2004 Usuda et al.
2004/0170986 A1 9/2004 Usuda et al.
2004/0170987 A1 9/2004 Usuda et al.
2004/0229305 A1 11/2004 Usuda et al.
2005/0014236 A1 1/2005 Matsuzaki et al.

FOREIGN PATENT DOCUMENTS

| EP | 0 082 485 | 6/1983 |
| EP | 0 472 869 | 3/1992 |
| FR | 2 612 937 | 9/1988 |
| JP | 63-240779 | 10/1988 |

OTHER PUBLICATIONS

J. K. Deb., et al., "Mini Review Plasmid of Corynebacteria", FEMS Microbiology Letters. 175 (1999), pp. 11-20, XP-001038258.
Broun et al., "Catalytic Plasticity of Fatty Acid Modification Enzymes Underlying Chemical Diversity of Plant Lipids", Science, 1998, vol. 282, pp. 1315-1317.
U.S. Appl. No. 09/868,338, filed Jun. 18, 2001, Kanno et al.
U.S. Appl. No. 09/926,299, filed Oct. 9, 2001, Gunji et al.
U.S. Appl. No. 09/636,458, filed Aug. 11, 2000, Matsuzaki et al.
U.S. Appl. No. 10/019,284, filed Jan. 2, 2002, Izui et al.
U.S. Appl. No. 10/933,280, filed Sep. 3, 2004, Nishio et al.

*Primary Examiner*—David Guzo
(74) *Attorney, Agent, or Firm*—Cermak & Kenealy, LLP; Shelly Guest Cermak

(57) ABSTRACT

A plasmid isolatable from *Corynebacterium thermoaminogenes*, which comprises a gene coding for a Rep protein having the amino acid sequence shown in SEQ ID NO: 8 or an amino acid sequence having homology of 90% or more to the amino acid sequence shown in SEQ ID NO: 8, and has a size of about 4.4 kb or about 6 kb, or a derivative thereof.

11 Claims, 6 Drawing Sheets

US 7,244,569 B2

PLASMID AUTONOMOUSLY REPLICABLE IN CORYNEFORM BACTERIA

This application is a divisional of Ser. No. 09/636,458, filed Aug. 11, 2000, now U.S. Pat. No. 6,905,819, which is hereby incorporated by reference. All documents cited herein, as well as the foreign priority document, JP1999-228391, filed Aug. 12, 1999, are also hereby incorporated by reference.

BACKGROUND OF THE INVENTION

The present invention relates to a novel plasmid derived from *Corynebacterium thermoaminogenes*. The plasmid of the present invention can be utilized for improving coryneform bacteria, which are used for producing useful substances such as L-amino acids.

Amino acids, including L-glutamic acid and L-lysine, are produced by fermentative methods using the coryneform bacteria, which generally belong to the genus *Brevibacterium*, *Corynebacterium*, or *Microbacterium*, or variant strains thereof (Amino Acid Fermentation, Gakkai Shuppan Center, pp. 195-215, 1986).

In the industrial fermentative production of amino acids, besides improving the yield relative to saccharides, shortening the culture time, improving the amino acid concentration, and so forth, increasing the culture temperature is an important technical factor that increases the economical efficiency. That is, the culture is usually performed at an optimum fermentation temperature, which is 31.5° C. for *Corynebacterium glutamicum*. After the culture is started, heat is generated during the fermentation, and hence amino acid production is markedly reduced if this heat output is not removed. Therefore, cooling equipment is required in order to maintain the optimum temperature of the culture broth. On the other hand, if the culture temperature can be elevated, it is then possible to decrease the energy required for cooling and the cooling equipment can be reduced in size.

Among coryneform bacteria, *Corynebacterium thermoaminogenes* has been isolated as a coryneform bacterium that can grow in higher temperatures (Japanese Patent Application Laid-open (Kokai) No. 63-240779). Whereas growth of *Corynebacterium glutamicum* is markedly suppressed at 40° C., *Corynebacterium thermoaminogenes* can grow at a temperature of about 40° C. or higher, and is therefore suitable for high temperature fermentation.

Currently, reliability of DNA recombination techniques is steadily improving in *Escherichia coli* and coryneform bacteria. To improve microorganisms using DNA recombinant techniques, plasmids derived from microorganisms belonging to other species, genus or broad host spectrum vectors are often used. However, plasmids native to the objective microorganism are generally used. In particular, when the optimum culture temperature for the objective microorganism to be improved is different from that of a microorganism of the same species or genus, it is preferable to use a plasmid native to the microorganism.

To date, plasmids derived from coryneform bacteria which have been obtained are pAM330 from *Brevibacterium lactofermentum* ATCC13869 (Japanese Patent Application Laid-open (Kokai) No. 58-67669), pBL1 from *Brevibacterium lactofermentum* ATCC21798 (Santamaria. R. et al., J. Gen. Microbiol., 130, pp.2237-2246, 1984), pHM1519 from *Corynebacterium glutamicum* ATCC13058 (Japanese Patent Application Laid-open (Kokai) No. 58-77895), pCG1 from *Corynebacterium glutamicum* ATCC31808 (Japanese Patent Application Laid-open (Kokai) No. 57-134500) and pGA1 from *Corynebacterium glutamicum* DSM58 (Japanese Patent Application Laid-open (Kokai) No. 9-2603011).

However, no plasmid native to *Corynebacterium thermoaminogenes* has been obtained at present.

SUMMARY OF THE INVENTION

An object of the present invention is to provide a plasmid which is useful for improving a coryneform bacterium that can grow at an elevated temperature, *Corynebacterium thermoaminogenes*.

The inventors of the present invention found that *Corynebacterium thermoaminogenes* AJ12340 (FERM BP-1539), AJ12308 (FERM BP-1540), AJ12309 (FERM BP-1541) and AJ12310 (FERM BP-1542) each harbored a cryptic plasmid native to each strain, and successfully isolated and identified each plasmid. Thus, they accomplished the present invention.

That is, the present invention provides a plasmid isolatable from *Corynebacterium thermoaminogenes*, which comprises a gene (rep gene) coding for a Rep protein which has the amino acid sequence shown in SEQ ID NO: 2, or an amino acid sequence which has homology of 90% or more to the foregoing amino acid sequence, and has a size of about 4.4 kb or about 6 kb, or a derivative thereof.

Examples of the aforementioned plasmids include a plasmid isolatable from *Corynebacterium thermoaminogenes* AJ12340 (FERM BP-1539), AJ12308 (FERM BP-1540) or AJ12310 (FERM BP-1542), which has a size of about 4.4 kb and is depicted in the restriction map shown in FIG. 1, and a plasmid isolatable from *Corynebacterium thermoaminogenes* AJ12309 (FERM BP-1541), which has a size of about 6 kb and is depicted in the restriction map shown in FIG. 2.

Specific examples of the aforementioned plasmid include a plasmid which comprises a gene coding for a Rep protein having the amino acid sequence shown in SEQ ID NO: 2, 4 or 6, and a plasmid which comprises a gene coding for a Rep protein having the amino acid sequence shown in SEQ ID NO: 8.

DETAILED DESCRIPTION OF THE INVENTION

The plasmid of the present invention can be isolated from *Corynebacterium thermoaminogenes* AJ12340 (FERM BP-1539), AJ12308 (FERM BP-1540), AJ12309 (FERM BP-1541) or AJ12310 (FERM BP-1542) according to a usual method for preparing a plasmid, such as the alkali method (Text for Bioengineering Experiments, Edited by the Society for Bioscience and Bioengineering, Japan, p. 105, Baifukan, 1992). FERM BP-1539 was deposited at the National Institute of Bioscience and Human-Technology, Agency of Industrial Science and Technology (postal code 305-8566, 1-3 Higashi 1-chome, Tsukuba-shi, Ibaraki-ken, Japan) on Mar. 13, 1987 and given an accession number of FERM P-9277, and was transferred to an international depository and deposited under the provisions of the Budapest Treaty on Oct. 27, 1987. FERM BP-1540, FERM BP-1541 and FERM BP-1542 were deposited at the aforementioned depository on Mar. 10, 1987 and given accession numbers of FERM P-9244, FERM P-9245 and FERM P-9246, and were transferred to an international depository and deposited under the provisions of the Budapest Treaty on Oct. 27, 1987.

The inventors of the present invention isolated and identified plasmids native to each of the aforementioned *Corynebacterium thermoaminogenes* AJ12308 (FERM BP-1540), AJ12310 (FERM BP-1542), AJ12340 (FERM BP-1539) and AJ12309 (FERM BP-1541), and designated them as pYM1, pYM2, pYM3 and pYM4, respectively. These plasmids exist as double-stranded circular DNA in a cell of *Corynebacterium thermoaminogenes*. The nucleotide sequence of the rep gene contained in pYM1 is shown in SEQ ID NO: 1, the nucleotide sequence of the rep gene contained in pYM2 is shown in SEQ ID NO: 3, the nucleotide sequence of the rep gene contained in pYM3 is shown in SEQ ID NO: 5, and the nucleotide sequence of the rep gene contained in pYM4 is shown in SEQ ID NO: 7. The amino acid sequences that can be encoded by the rep genes contained in these plasmids are shown in SEQ ID NOS: 2, 4, 6 and 8. pYM1, pYM2 and pYM3 each have a size of about 4.4 kb. pYM4 has a size of about 6 kb.

Figure 1:
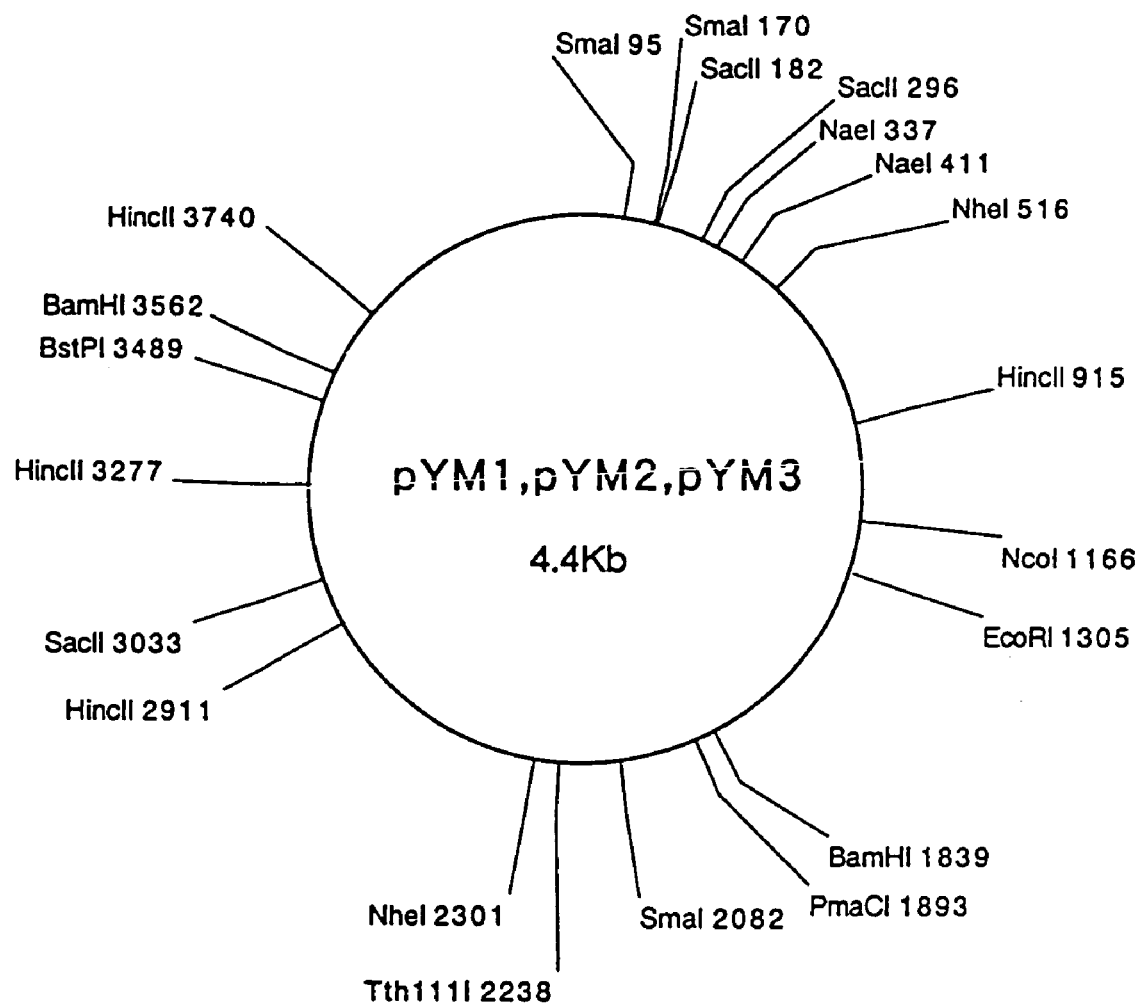
FIG. 1 is a restriction map of the plasmids pYM1, pYM2 and pYM3 of the present invention.
Figure 2:
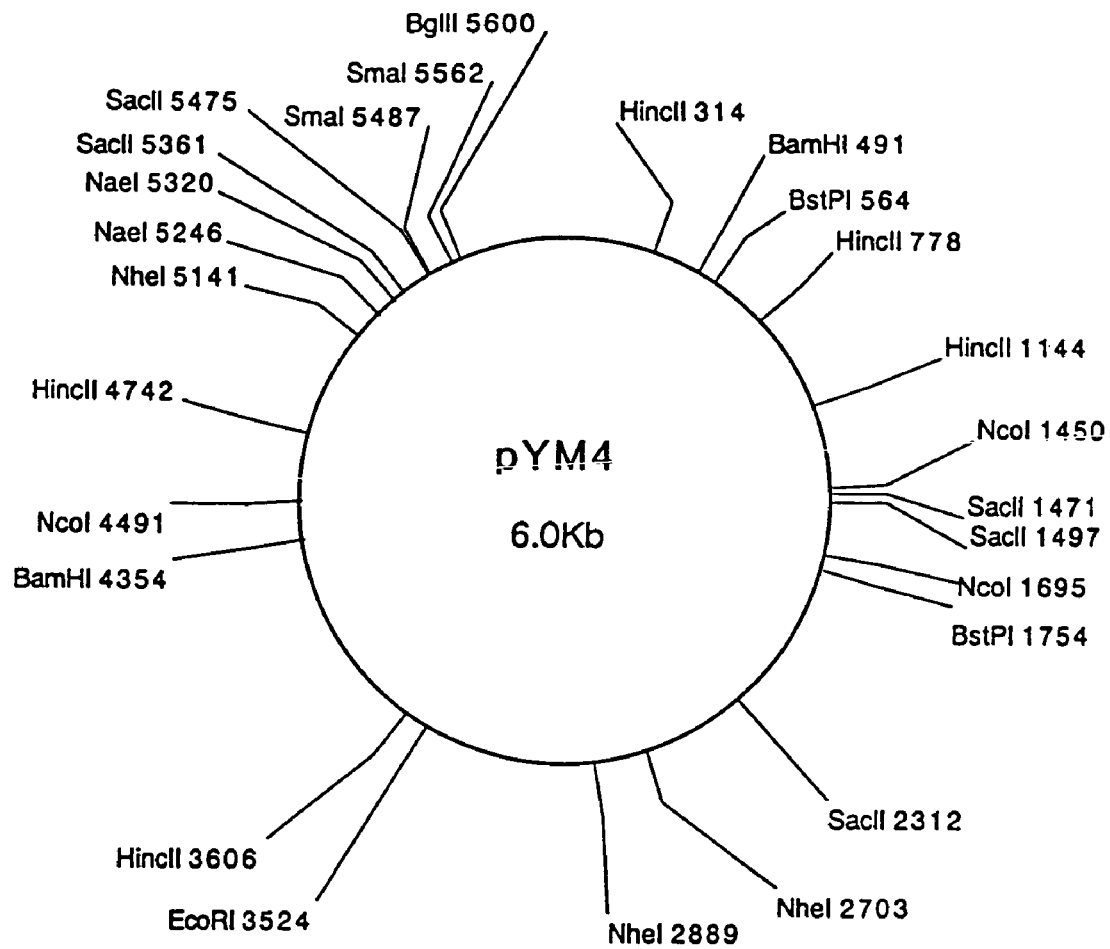
FIG. 2 is a restriction map of the plasmid pYM4 of the present invention.

The numbers and sizes of fragments that can be obtained when pYM1, pYM2 and pYM3 are digested with typical restriction enzymes are shown in Table 1. The numbers and sizes of fragments that can be obtained when pYM4 is digested with typical restriction enzymes are shown in Table 2. Further, a restriction map of pYM1, pYM2 and pYM3 is shown in FIG. 1, and a restriction map of pYM4 is shown in FIG. 2.

TABLE 1

| Restriction enzyme | Number of digestion site | DNA fragment (kb) |
|---|---|---|
| BglII | 0 | — |
| BamHI | 2 | 1.8, 2.6 |
| BstPI | 1 | 4.4 |
| EcoRI | 1 | 4.4 |
| HincII | 4 | 0.3, 0.5, 2.0, 1.6 |
| HindIII | 0 | — |
| KpnI | 0 | — |
| NaeI | 2 | 0.1, 4.3 |
| NcoI | 1 | 4.4 |
| NheI | 2 | 1.8, 2.6 |
| PmaCI | 1 | 4.4 |
| SacI | 0 | — |
| SalI | 0 | — |
| SacII | 3 | 0.1, 1.4, 2.9 |
| SmaI | 3 | 0.1, 1.8, 2.5 |
| SphI | 0 | — |
| Tth111I | 1 | 4.4 |
| XbaI | 0 | — |

TABLE 2

| Restriction enzyme | Number of digestion site | DNA fragment (kb) |
|---|---|---|
| BglII | 1 | 6.0 |
| BamHI | 2 | 3.8, 2.2 |
| BstPI | 2 | 1.2, 4.8 |
| EcoRI | 1 | 6.0 |
| HincII | 4 | 0.3, 0.4, 1.2, 1.7, 2.4 |
| HindIII | 0 | — |
| KpnI | 0 | — |
| NaeI | 2 | 0.1, 5.9 |

TABLE 2-continued

| Restriction enzyme | Number of digestion site | DNA fragment (kb) |
|---|---|---|
| NcoI | 3 | 0.2, 2.8, 3.0 |
| NheI | 3 | 0.1, 2.3, 3.6 |
| PmaCI | 0 | — |
| SacI | 0 | — |
| SalI | 0 | — |
| SacII | 5 | 0.1, 0.2, 0.9, 1.8, 3.0 |
| SmaI | 2 | 0.1, 5.9 |
| SphI | 0 | — |
| Tth111I | 0 | — |
| XbaI | 0 | — |

Determination of the nucleotide sequence of the plasmids of the present invention revealed that pYM1, pYM2, and pYM3 each contain 4368 bp, 4369 bp and 4369 bp, respectively, have substantially the same structure, and have homology of 99.9% to one another on the nucleotide sequence level. Further, pYM4 contains 5967 bp and has extremely high homology to pYM1, pYM2 and pYM3 in the about 4.4 kb region, while pYM4 only has homology of about 81% when compared as a whole.

The plasmids contain respective rep genes which have high homology to one another. Homology was compared for the amino acid sequences of the Rep proteins encoded by the rep genes (SEQ ID NOS: 2, 4, 6 and 8) and the amino acid sequences of the Rep proteins encoded by rep genes of known plasmids derived from coryneform bacteria. Homology of 99% or more was observed among pYM1, pYM2 and pYM3, and homology of 81.91% was observed between pYM2 and pYM4. On the other hand, they showed no homology to the known plasmid pAM330 of a coryneform bacterium, and they showed homology of 80% or less to pGA1 and pCG1. The results are shown in Table 3. Thus, the plasmid of the present invention and the known plasmids of coryneform bacteria are distinguishable based on the homology of the Rep protein.

The homology is calculated according to the method described in Takashi, K. and Gotoh, O., J. Biochem., 92, 1173-1177 (1984).

TABLE 3

| | Homology of amino acid sequences of Rep protein encoded by various plasmids | | | |
|---|---|---|---|---|
| | PYM2 | pYM4 | pGA1 | pCG1 |
| PYM2 | — | 81.91% | 68.01% | 70.73% |
| PYM4 | — | — | 69.39% | 70.23% |
| PGA1 | — | — | — | 75.31% |
| PCG1 | — | — | — | — |

Since the plasmid of the present invention can sufficiently replicate in cells of coryneform bacteria, including *Corynebacterium thermoaminogenes*, the genetic information of a foreign gene can be expressed in a host microorganism by inserting the foreign gene at any site in the plasmid, or the derivative thereof, and transforming the host microorganism with the resulting recombinant plasmid.

Examples of coryneform bacteria are listed below.
*Corynebacterium acetoacidophilum*
*Corynebacterium acetoglutamicum*
*Corynebacterium callunae*
*Corynebacterium glutamicum*
*Corynebacterium thermoaminogenes*
*Corynebacterium lilium* (*Corynebacterium glutamicum*)
*Corynebacterium melassecola*

*Brevibacterium divaricatum* (*Corynebacterium glutamicum*)

*Brevibacterium lactofermentum* (*Corynebacterium glutamicum*)

*Brevibacterium saccharolyticum*

*Brevibacterium immariophilum*

*Brevibacterium roseum*

*Brevibacterium flavum* (*Corynebacterium glutamicum*)

*Brevibacterium thiogenitalis*

A "derivative" of the plasmid of the present invention means a plasmid composed of a part of the plasmid of the present invention, or the plasmid of present invention and another DNA sequence. The "part of a plasmid" means a part containing a region essential for autonomous replication of the plasmid. The plasmid of the present invention can replicate in a host microorganism even if a region other than the region essential for the autonomous replication of the plasmid (replication control region), that is, the region other than the region containing the replication origin and genes necessary for the replication, is deleted. In addition, a plasmid having such a deletion will have a smaller size. Therefore, a plasmid having such a deletion is preferred for use as a vector. Furthermore, if a marker gene, such as a drug resistance gene, is inserted into the plasmid of the present invention or a part thereof, it becomes easy to detect transformants thanks to the phenotype of the marker gene in the transformants. Examples of such a marker gene that can be used in the host include chloramphenicol resistance gene, kanamycin resistance gene, streptomycin resistance gene, tetracycline resistence gene, trimethoprim resistance gene, erythromycin resistance gene, and so forth.

Furthermore, if the plasmid of the present invention is made as a shuttle vector, which is autonomously replicable in coryneform bacteria and other bacteria such as *Escherichia coli*, by ligating the plasmid of the present invention or a part thereof with a plasmid autonomously replicable in the other bacteria such as *Escherichia coli* or a part thereof containing a replication control region thereof, manipulations can be performed using *Escherichia coli*, such as preparation of plasmid and preparation of recombinant plasmid containing a target gene. Examples of a plasmid autonomously replicable in *Escherichia coli* include, for example, pUC19, pUC18, pBR322, pHSG299, pHSG298, pHSG399, pHSG398, RSF110, pMW119, pMW118, pMW219, pMW218, and so forth.

Although pYM1, pYM2, pYM3 and pYM4 are characterized by the restriction maps shown in FIGS. 1 and 2, it is not necessarily required that the plasmid of present invention have these restriction maps, and any restriction site may be deleted as long as such deletion does not affect the autonomous replication ability. Furthermore, the plasmid of the present invention may contain a restriction site that is not contained in pYM1, pYM2, pYM3 and pYM4.

The derivative of the plasmid as described above can be constructed in the same manner as the conventionally known construction of cloning vectors, expression vectors and so forth. In order to construct the derivative, it is preferable to determine the nucleotide sequences of pYM1, pYM2, pYM3 and pYM4. The nucleotide sequences can be determined by known methods, such as the dideoxy method.

In order to insert a foreign gene into the plasmid or the derivative thereof of the present invention, it is convenient to insert it into a restriction site of the plasmid or the derivative thereof. A restriction site which is present as a single digestion site is preferred. In order to insert a foreign gene, the plasmid and the source of the foreign gene, such as genomic DNA, can be partially or fully digested with one or more restriction enzymes that provide the same cohesive ends, e.g., the same restriction enzyme, and they can be ligated under suitable conditions. They may also be blunt-end ligated.

For the preparation of plasmid DNA, digestion and ligation of DNA, transformation and so forth, methods well-known to those skilled in the art may be employed. Such methods are described in Sambrook, J., Fritsch, E. F., and Maniatis, T., "Molecular Cloning: A Laboratory Manual, Second Edition", Cold Spring Harbor Laboratory Press (1989), and so forth.

According to the present invention, a novel plasmid derived from *Corynebacterium thermoaminogenes* is provided as described above.

EXAMPLES

Hereinafter, the present invention will be explained in more detail with reference to the following examples.

Example 1

Isolation and Characterization of Plasmids from *Corynebacterium Thermoaminogenes* (FERM BP-1539, FERM BP-1540, FERM BP-1541, FERM BP-1542)

*Corynebacterium thermoaminogenes* AJ12340 (FERM BP-1539), AJ12308 (FERM BP-1540), AJ12309 (FERM BP-1541) and AJ12310 (FERM BP-1542) were cultured for 12 hours in CM2B liquid medium (Bacto-trypton (Difco): 1%, Bacto-yeast-extract (Difco): 1%, NaCl: 0.5%, biotin: 10 μg/L), and plasmid DNA fractions were obtained by the alkali method (Text for Bioengineering Experiments, Edited by the Society for Bioscience and Bioengineering, Japan, p.105, Baifukan, 1992). When these fractions were analyzed by agarose gel electrophoresis (Sambrook, J., Fritsch, E. F., and Maniatis, T., "Molecular Cloning: A Laboratory Manual, Second Edition", Cold Spring Harbor Laboratory Press (1989)), DNA bands were detected for all of the fractions, and hence it was demonstrated that the aforementioned strains harbored plasmids. The plasmids prepared from FERM BP-1540, FERM BP-1542 and FERM BP-1539 were designated as pYM1, pYM2 and pYM3, respectively. The plasmid prepared from FERM BP-1541 was designated as pYM4. The plasmids pYM1, pYM2 and pYM3 each had a length of about 4.4 kb, and the plasmid pYM4 had a length of about 6.0 kb.

The plasmids pYM1, pYM2, pYM3 and pYM4 were digested with restriction enzymes BglII, BamHI, BstPI, EcoRI, HincII, HindIII, KpnI, NaeI, NcoI, NheI, PmaCI, SacI, SacII, SalI, SmaI, SphI, Tth111I and XbaI (produced by Takara Co.), and the lengths of the produced DNA fragments were measured by agarose gel electrophoresis. The electrophoresis was performed at 100 V/cm and a constant voltage for several hours by using a 0.8% agarose gel. λ phage DNA (Takara Shuzo) digested with a restriction enzyme HindIII was used as molecular weight markers. The results obtained for pYM1, pYM2 and pYM3 are shown in Table 1. The results obtained for pYM4 are shown in Table 2. The restriction map of pYM1, pYM2 and pYM3 is shown in FIG. 1, and the restriction map of pYM4 is shown in FIG. 2, which were prepared based on the above results.

The results of nucleotide sequencing of pYM1, pYM2, pYM3 and pYM4 by the dideoxy method are shown in SEQ ID NOS: 1, 3, 5 and 7 respectively.

Example 2

Construction of the Shuttle Vector pYMFK Containing the Km Resistance Gene derived from *Streptococcus Faecalis*

Regions necessary for efficient replication of pYM2 in coryneform bacteria include an AT-rich region upstream from rep and a region which affects copy number downstream from rep, besides the region coding for rep.

Therefore, in order to obtain a shuttle vector that can replicate in coryneform bacteria and *E. coli* without impairing the replication ability of pYM2, a region enabling autonomous replication in *E. coli* and a selection marker were inserted into sites in the vicinity of the BstPI site of pYM2.

First, a vector having a drug resistance gene of *S. faecalis* was constructed. The kanamycin resistance gene of *S. faecalis* was amplified by PCR from a known plasmid containing that gene. The nucleotide sequence of the kanamycin resistance gene of *S. faecalis* has already been elucidated (Trieu-Cuot, P. and Courvalin, P., Gene, 23 (3), pp.331-341 (1983)). Based on this sequence, primers having the nucleotide sequences shown as SEQ ID NOS: 16 and 17 were synthesized, and PCR was performed using pDG783 (Anne-Marie Guerout-Fleury et al., Gene, 167, pp.335-337 (1995)) as a template to amplify a DNA fragment containing the kanamycin resistance gene and its promoter. The above DNA fragment was purified by using SUPREC02 produced by Takara Shuzo Co., Ltd., completely digested with restriction enzymes HindIII and HincII, and blunt-ended. The blunt-ending was performed by Blunting Kit produced by Takara Shuzo Co., Ltd. This DNA fragment and an amplification product obtained by PCR with primers having the nucleotide sequences shown as SEQ ID NOS: 18 and 19, and pHSG399 (see S. Takeshita et al., Gene, 61, pp.63-74 (1987)) as a template, and purification and blunt-ending were mixed and ligated. The ligation reaction was performed by using DNA Ligation Kit ver.2 produced by Takara Shuzo Co., Ltd. Competent cells of *Escherichia coli* JM109 (produced by Takara Shuzo Co., Ltd.) were transformed with the ligated DNA, and cultured overnight in L medium (10 g/L of Bacto trypton, 5 g/L of Bacto yeast extract, 5 g/L of NaCl, and 15 g/L of agar, pH 7.2) containing 10 μg/ml of IPTG (isopropyl-β-D-thiogalactopyranoside), 40 μg/ml of X-Gal (5-bromo-4-chloro-3-indolyl-β-D-galactoside) and 25 μg/ml of kanamycin. Then, the formed blue colonies were subjected to single colony isolation to obtain transformants.

Figure 6:
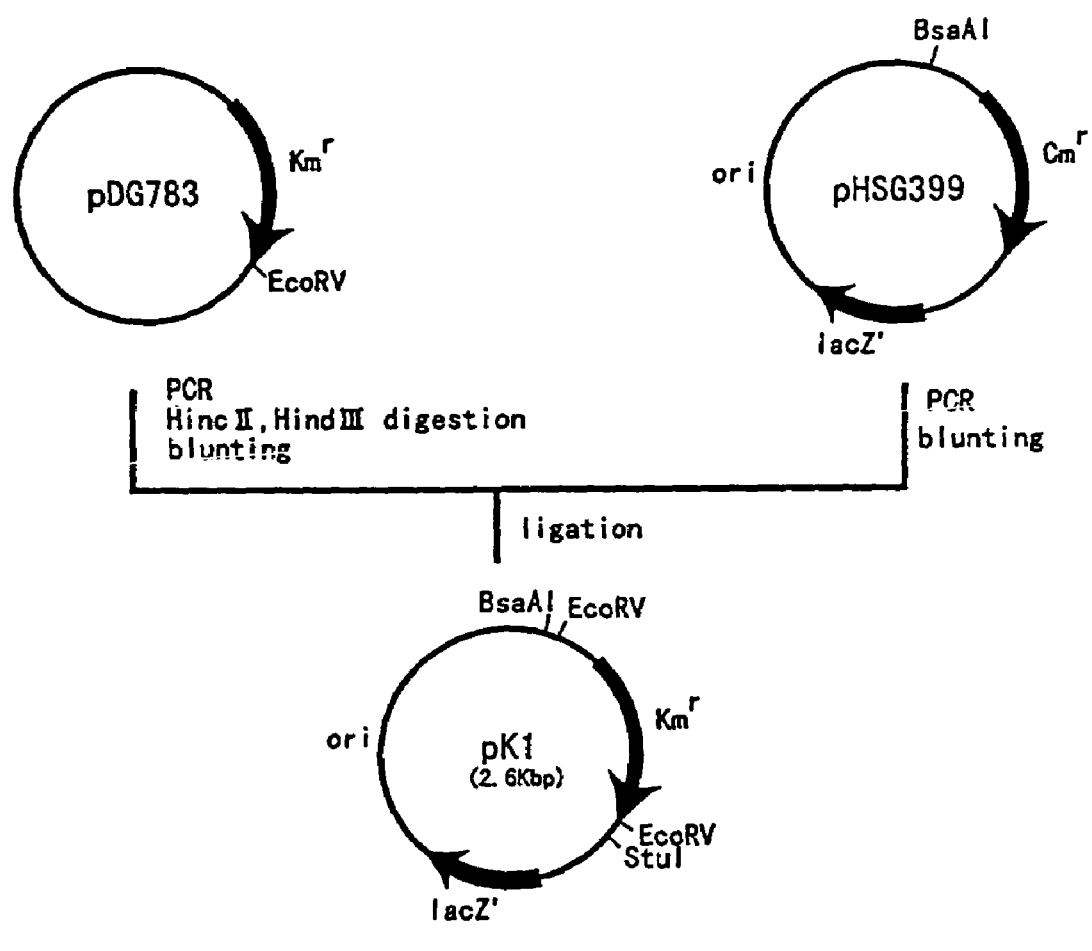
FIG. 6 shows construction of pK1.

Plasmids were prepared from the transformants using the alkaline method (Text for Bioengineering Experiments, Edited by the Society for Bioscience and Bioengineering, Japan, p.105, Baifukan, 1992), and restriction maps were prepared. A plasmid having a restriction map equivalent to that shown at a lower position in FIG. 6 was designated as pK1. This plasmid is stably harbored in *Escherichia coli*, and imparts kanamycin resistance to a host. Moreover, since it contains the lacZ' gene, it is suitable for use as a cloning vector.

Then, a region containing the replication origin was amplified by Pyrobest-Taq (Takara Shuzo Co., Ltd.) using pYM2 extracted from *C. thermoaminogenes* AJ12310 (FERM BP-1542) as a template (The entire nucleotide sequence of pYM2 is shown in SEQ ID NO: 9.) and the following primers were prepared based on a sequence in pYM2 near the BstPI site:

S1: 5'-AAC CAG GGG GAG GGC GCG AGG C-3' (SEQ ID NO: 10)

S3: 5'-TCT CGT AGG CTG CAT CCG AGG CGG GG-3' (SEQ ID NO: 11)

The reaction conditions were 94° C. for 5 minutes, followed by a cycle of 98° C. for 20 seconds, and 68° C. for 4 minutes, which was repeated for 30 cycles, and 72° C. for 4 minutes. After the reaction, the mixture was stored at 4° C.

The resulting amplified fragment was purified using MicroSpin TM S-400 HR columns produced by Amersham Pharmacia Biotech Co., blunt-ended using DNA Blunting Kit produced by Takara Shuzo Co., Ltd., and then ligated to pK1, which had been treated with HincII using DNA Ligation Kit. ver. 2 produced by Takara Shuzo Co., Ltd. Competent cells of *Escherichia coli* JM109 (produced by Takara Shuzo) were transformed with the ligated DNA to obtain transformant strains.

Figure 3:
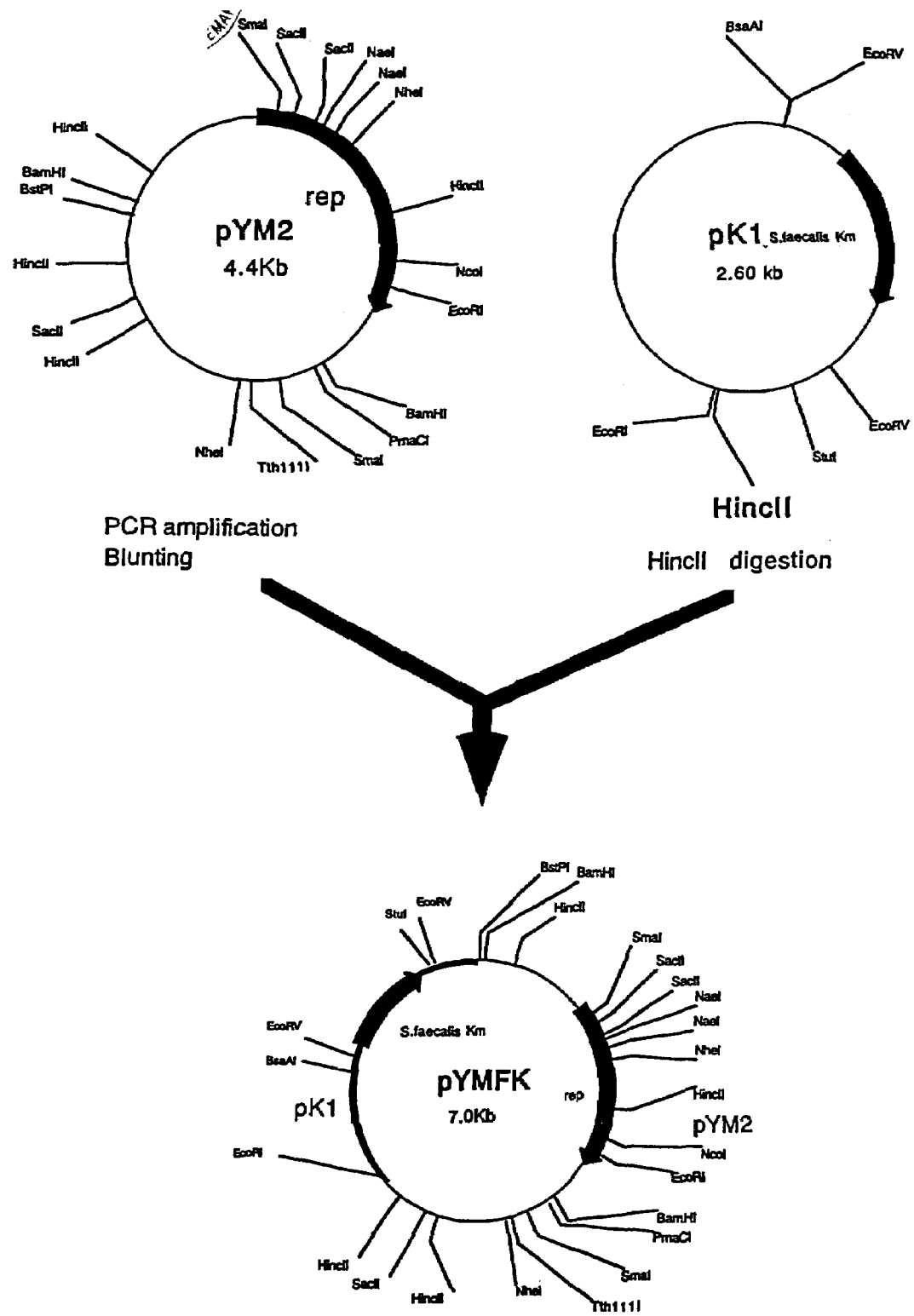
FIG. 3 shows construction of pYMFK.

Plasmids were prepared from the transformant strains using the alkali method (Text for Bioengineering Experiments, Edited by the Society for Bioscience and Bioengineering, Japan, p.105, Baifukan, 1992) and restriction maps of the plasmids were prepared. A restriction map equivalent to that shown at a lower position in FIG. 3 was designated as pYMFK. pYMFK had a size of about 7.0 kb, and was able to autonomously replicate in *E. coli* and coryneform bacteria and impart Km resistance to a host.

Example 3

Construction of pYMK Containing Km Resistance Gene Derived from Tn903

A region containing the replication origin was amplified in the same manner as in Example 2 by using pYM2 extracted from *C. thermoaminogenes* AJ12310 (FERM BP-1542) as a template and the following primers:

```
S1XbaI:  5'-GCT CTA GAG CAA CCA GGG GGA GGG CGC GAG GC-3'   (SEQ ID NO: 12)

S3XbaI:  5'-GCT CTA GAG CTC TCG TAG GCT GCA TCG GAG GCG GGG-3'  (SEQ ID NO: 13)
```

The obtained amplified fragment was purified by using MicroSpin TM S-400 HR columns produced by Amersham Pharmacia Biotech Co., digested with a restriction enzyme XbaI produced by Takara Shuzo Co., Ltd., and then ligated to a fragment obtained by fully digesting pHSG299 (Takara Shuzo Co., Ltd.) with XbaI by using DNA Ligation Kit. ver. 2 produced by Takara Shuzo Co., Ltd. Competent cells of *Escherichia coli* JM109 (produced by Takara Shuzo) were transformed with the ligated DNA to obtain transformant strains.

Figure 4:
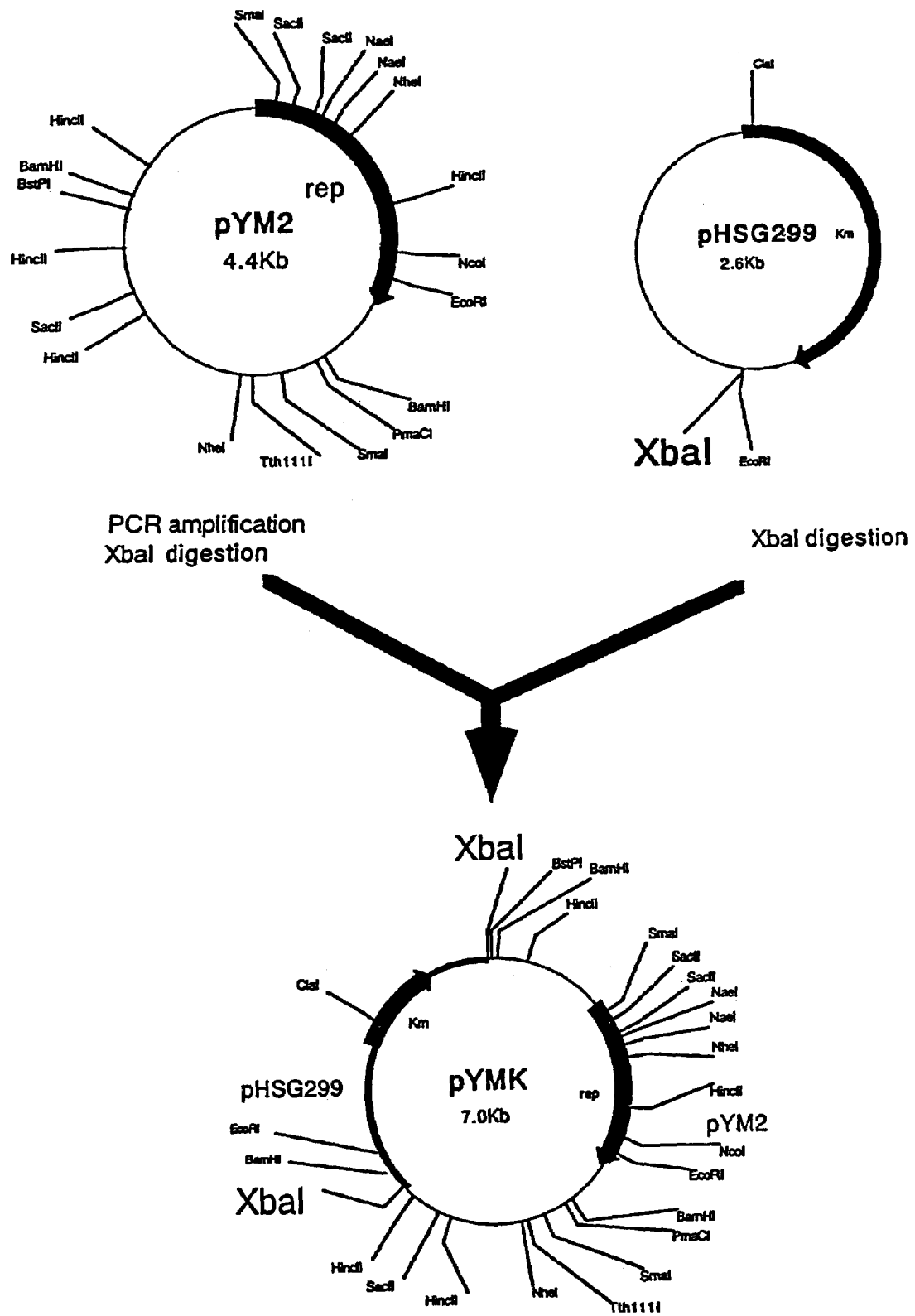
FIG. 4 shows construction of pYMK.

Plasmids were prepared from the transformant strains using the alkali method (Text for Bioengineering Experiments, Edited by the Society for Bioscience and Bioengineering, Japan, p.105, Baifikan, 1992) and restriction maps of the plasmids were prepared. A restriction map equivalent to that shown at a lower position in FIG. 4 was designated as pYMK. pYMK had a size of about 7.0 kb, and was able to autonomously replicate in *E. coli* and coryneform bacteria and impart Km resistance to a host.

Example 4

Construction of Shuttle Vector pYMC Containing Cm Resistance Gene Derived from Tn9

A region containing the replication origin was amplified in the same manner as in Example 2 by using pYM2 extracted from *C. thermoaminogenes* AJ12310 (FERM BP-1542) as a template and the following primers:

S1XbaI: 5'-GCT CTA GAG CAA CCA GGG GGA GGG CGC GAG GC-3'        (SEQ ID NO: 14)

S3XbaI: 5'-GCT CTA GAG CTC TCG TAG GCT GCA TCG GAG GCG GGG-3' (SEQ ID NO: 15)

The above DNA was purified by using MicroSpin TM S-400 HR columns produced by Amersham Pharmacia Biotech Co., digested with a restriction enzyme XbaI produced by Takara Shuzo Co., Ltd., and then ligated to a fragment obtained by treating pHSG399 (Takara Shuzo Co., Ltd.) with XbaI using DNA Ligation Kit. ver. 2 produced by Takara Shuzo Co. Ltd. Competent cells of *Escherichia coli* JM109 (produced by Takara Shuzo) were transformed with the ligated DNA to obtain transformant strains.

Figure 5:
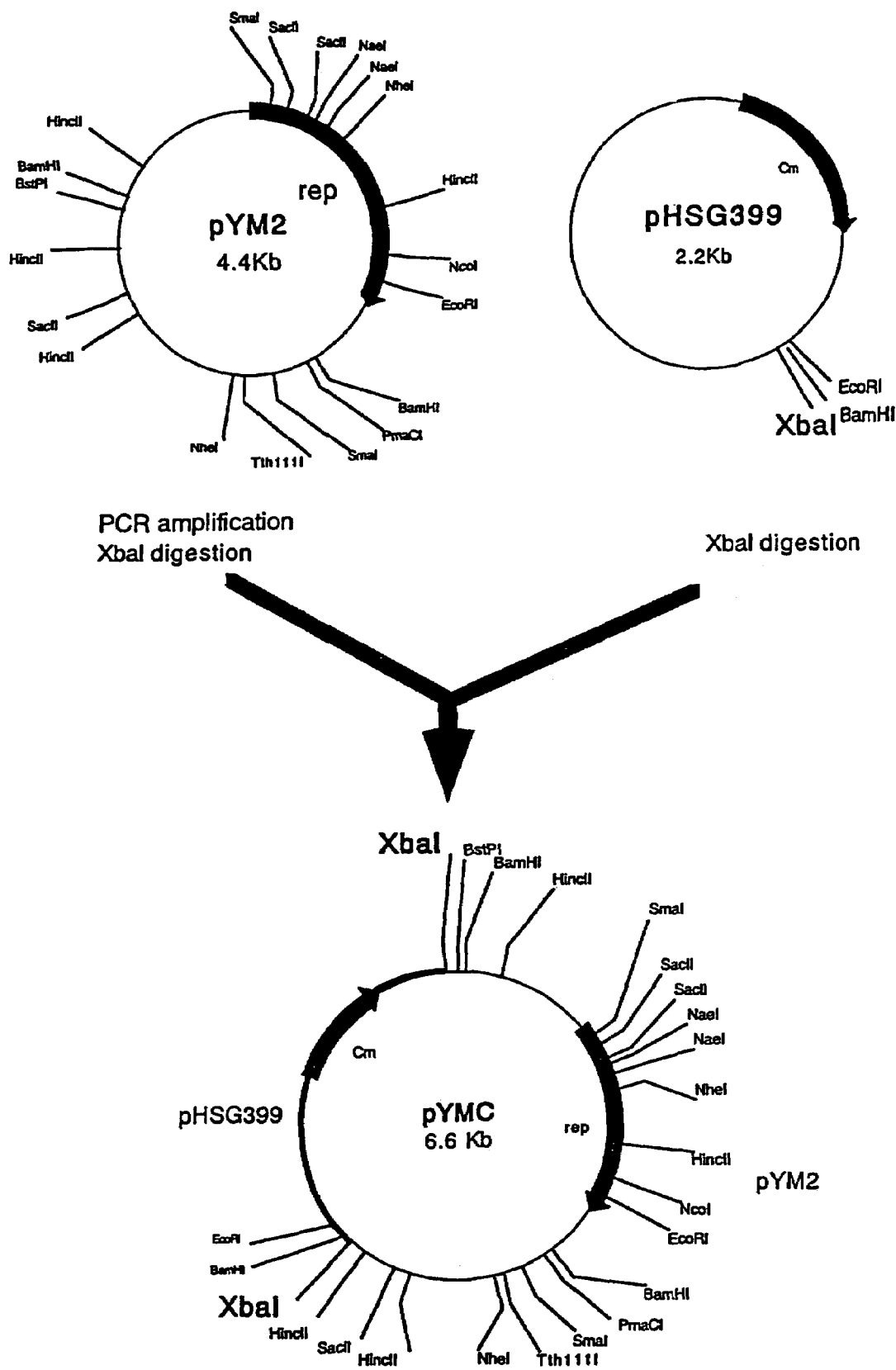
FIG. 5 shows construction of pYMC.

Plasmids were prepared from the transformant strains using the alkali method (Text for Bioengineering Experiments, Edited by the Society for Bioscience and Bioengineering, Japan, p. 105, Baifukan, 1992) and restriction maps of the plasmids were prepared. One showing a restriction map equivalent to that shown at a lower position in FIG. 5 was designated as pYMC. pYMC had a size of about 6.6 kb, and was able to autonomously replicate in *E. coli* and coryneform bacteria and impart Cm resistance to a host.

---

We claim:

1. An isolated plasmid comprising a gene, said gene encoding a polypeptide having Rep protein activity and, said polypeptide comprising an amino acid sequence that is at least 90% homologous to the amino acid sequence of SEQ ID NO: 8.

2. The plasmid according to claim 1, wherein said polypeptide comprises an amino acid sequence that is at least 99% homologous to the amino acid sequence of SEQ ID NO: 8.

3. The plasmid according to claim 1, wherein said polypeptide comprises the amino acid sequence of SEQ ID NO: 8.

4. The plasmid according to claim 1, wherein said plasmid is isolated from *Corynebacterium thermoaminogenes* AJ12309.

5. The plasmid according to claim 1, which has the restriction map shown in FIG. 2.

6. The plasmid according to claim 1, wherein said gene is obtained from a plasmid having the restriction map shown in FIG. 2.

7. The method of isolating the plasmid according to claim 1, comprising (A) culturing a *Corynebacteriuin thermoaminogenes* in a culture medium, (B) obtaining fractions by an alkali method, and (C) isolating said plasmid.

8. The method according to claim 7, further comprising analyzing the fractions by agarose gel electrophoresis.

9. An isolated polynucleotide comprising a ucleic acid sequence that encodes a polypeptide having Rep protein activity and, said polypeptide comprising an amino acid sequence that is at least 90% homologous to the amino acid sequence of SEQ ID NO. 8.

10. The polynucleotide according to claim 9, wherein said polypeptide comprises an amino acid sequence that is at least 99% homologous to the amino acid sequence of SEQ ID NO:8.

11. The polynucleotide according to claim 9, wherein said polypeptide comprises the amino acid sequence of SEQ ID NO:8.

* * * * *

SEQUENCE LISTING

<160> NUMBER OF SEQ ID NOS: 20

<210> SEQ ID NO 1
<211> LENGTH: 1479
<212> TYPE: DNA
<213> ORGANISM: Corynebacterium thermoaminogenes
<220> FEATURE:
<221> NAME/KEY: CDS
<222> LOCATION: (1)..(1476)
<223> OTHER INFORMATION:

<400> SEQUENCE: 1

```
atg act cta gcg gat tcg cca gga aca tac aca gca gat gcg tgg aat        48
Met Thr Leu Ala Asp Ser Pro Gly Thr Tyr Thr Ala Asp Ala Trp Asn
1               5                   10                  15 tac tcc act gat ctg ttc gac acc cac cct gag ctg gct tta cgc tcc        96
Tyr Ser Thr Asp Leu Phe Asp Thr His Pro Glu Leu Ala Leu Arg Ser
                20                  25                  30 cgg ggt tgg aat cac cag gac gcc gcc gag ttc ctg gcc cac ctg gat       144
Arg Gly Trp Asn His Gln Asp Ala Ala Glu Phe Leu Ala His Leu Asp
            35                  40                  45 cgc agc atg ttt cac ggg tgc ccc acc cgg gat ttc tcc gcg gcc tgg       192
Arg Ser Met Phe His Gly Cys Pro Thr Arg Asp Phe Ser Ala Ala Trp
        50                  55                  60 gtc aaa gac ccg gaa acc gga gaa acc cgc ccc aag ctg cac aga gtt       240
Val Lys Asp Pro Glu Thr Gly Glu Thr Arg Pro Lys Leu His Arg Val
65                  70                  75                  80 ggc acc cgc tca ctt tcc cgg tgc cag tac gtt gcc ctg acc cac ccg       288
Gly Thr Arg Ser Leu Ser Arg Cys Gln Tyr Val Ala Leu Thr His Pro
                85                  90                  95 cag cgc tcc gcg gtg ctg gtc tta gac atc gac atc ccc agc cac cag       336
Gln Arg Ser Ala Val Leu Val Leu Asp Ile Asp Ile Pro Ser His Gln
                100                 105                 110 gcc ggc ggg aac atc gag cac ctt cac ccg cag gtg tac gcc acc ttg       384
Ala Gly Gly Asn Ile Glu His Leu His Pro Gln Val Tyr Ala Thr Leu
            115                 120                 125 gag cgt tgg gca cgg gtg gag aaa gcg ccg gcc tgg atc ggg gtg aac       432
Glu Arg Trp Ala Arg Val Glu Lys Ala Pro Ala Trp Ile Gly Val Asn
        130                 135                 140 ccg ttg tcg gga aag tgc cag ctc atc tgg tgc att gac ccg gtg ttc       480
Pro Leu Ser Gly Lys Cys Gln Leu Ile Trp Cys Ile Asp Pro Val Phe
145                 150                 155                 160 gcc gcc gag ggc acc acc agc tcg aac acc cgc ctg cta gcg gcc acc       528
Ala Ala Glu Gly Thr Thr Ser Ser Asn Thr Arg Leu Leu Ala Ala Thr
                165                 170                 175
```

| | | |
|---|---|---|
| acc gag gaa atg acc cgt gtg ttc ggc gct gac cag gca ttt tcc cac<br>Thr Glu Glu Met Thr Arg Val Phe Gly Ala Asp Gln Ala Phe Ser His<br>               180                          185                        190 | 576 |

```
acc gag gaa atg acc cgt gtg ttc ggc gct gac cag gca ttt tcc cac      576
Thr Glu Glu Met Thr Arg Val Phe Gly Ala Asp Gln Ala Phe Ser His
            180                 185                 190 cgg ctg agc cgg tgg ccg ctg cat gtt tct gat gat ccg acc gcg tac      624
Arg Leu Ser Arg Trp Pro Leu His Val Ser Asp Asp Pro Thr Ala Tyr
                195                 200                 205 tcc tgg cac tgc cag cac aac cga gtc gat att ctt gat gag ctg atg      672
Ser Trp His Cys Gln His Asn Arg Val Asp Ile Leu Asp Glu Leu Met
        210                 215                 220 gag gta gcc cgc acg atg acc gga tca aaa aag ccc aga gag cac gct      720
Glu Val Ala Arg Thr Met Thr Gly Ser Lys Lys Pro Arg Glu His Ala
225                 230                 235                 240 cac cag gag ttt tcc agc ggt cgg gca cgg atc gaa gcc gcg cgg aaa      768
His Gln Glu Phe Ser Ser Gly Arg Ala Arg Ile Glu Ala Ala Arg Lys
                245                 250                 255 gcc acc gca gag gcc aaa gcg ctt gcc gcc ttg gac gcc acg ctg cct      816
Ala Thr Ala Glu Ala Lys Ala Leu Ala Ala Leu Asp Ala Thr Leu Pro
        260                 265                 270 acg gcg ctg gag gca tca ggc gat ctc att gac ggg gtg cgg gtg ttg      864
Thr Ala Leu Glu Ala Ser Gly Asp Leu Ile Asp Gly Val Arg Val Leu
    275                 280                 285 tgg gca gca gag ggg cgt gca gcc cgt gat gag aca gcg ttt cgc cat      912
Trp Ala Ala Glu Gly Arg Ala Ala Arg Asp Glu Thr Ala Phe Arg His
290                 295                 300 gcg ttg acc gtg ggt tat cag ctt aaa gcc gca ggt gaa cgc ctg aaa      960
Ala Leu Thr Val Gly Tyr Gln Leu Lys Ala Ala Gly Glu Arg Leu Lys
305                 310                 315                 320 gat gcc aag atc att gat gcg tat gag cgt gcc tac aac gtc gcc cag     1008
Asp Ala Lys Ile Ile Asp Ala Tyr Glu Arg Ala Tyr Asn Val Ala Gln
                325                 330                 335 gcg gtg gga gct gat ggg cgt gaa ccg gat ctg cct gcc atg cgt gat     1056
Ala Val Gly Ala Asp Gly Arg Glu Pro Asp Leu Pro Ala Met Arg Asp
            340                 345                 350 cgt cag acg atg gcc cgc cgt gtg cgc gcc tac gtc gcc aaa ggc cag     1104
Arg Gln Thr Met Ala Arg Arg Val Arg Ala Tyr Val Ala Lys Gly Gln
        355                 360                 365 ccc acg gtc agc gcc agg agc aca cag acc cag agc agt cgg ggc cgg     1152
Pro Thr Val Ser Ala Arg Ser Thr Gln Thr Gln Ser Ser Arg Gly Arg
    370                 375                 380 aaa gcc ctg gcc acc atg ggc cgc aga ggc ggg caa aaa gcc gct gaa     1200
Lys Ala Leu Ala Thr Met Gly Arg Arg Gly Gly Gln Lys Ala Ala Glu
385                 390                 395                 400 cgc tgg aaa acc gat cct aac ggc aaa tac gcc caa gaa aac cgc caa     1248
Arg Trp Lys Thr Asp Pro Asn Gly Lys Tyr Ala Gln Glu Asn Arg Gln
                405                 410                 415 cga ctc gaa gct gca aac aag cga cgt caa gtc agc tgg aac aaa tac     1296
Arg Leu Glu Ala Ala Asn Lys Arg Arg Gln Val Ser Trp Asn Lys Tyr
            420                 425                 430 gcg agc acg aat tct ggc tac ggt ttc cga cac gta tgg gcc agc ttg     1344
Ala Ser Thr Asn Ser Gly Tyr Gly Phe Arg His Val Trp Ala Ser Leu
        435                 440                 445 gaa aaa tgc cta cgc gac gag caa atc atg gaa gaa aca ggg ctt tca     1392
Glu Lys Cys Leu Arg Asp Glu Gln Ile Met Glu Glu Thr Gly Leu Ser
    450                 455                 460 gaa aaa tgc cta cgc gac gag caa atc atg gaa gaa aca ggg ctt tca     1440
Glu Lys Cys Leu Arg Asp Glu Gln Ile Met Glu Glu Thr Gly Leu Ser
465                 470                 475                 480 tgc caa atc ctt agg ggg gct cac gcc gta gac aga taa                 1479
Cys Gln Ile Leu Arg Gly Ala His Ala Val Asp Arg
```

485          490

<210> SEQ ID NO 2
<211> LENGTH: 492
<212> TYPE: PRT
<213> ORGANISM: Corynebacterium thermoaminogenes

<400> SEQUENCE: 2

Met Thr Leu Ala Asp Ser Pro Gly Thr Tyr Thr Ala Asp Ala Trp Asn
1               5                   10                  15

Tyr Ser Thr Asp Leu Phe Asp Thr His Pro Glu Leu Ala Leu Arg Ser
            20                  25                  30

Arg Gly Trp Asn His Gln Asp Ala Ala Glu Phe Leu Ala His Leu Asp
        35                  40                  45

Arg Ser Met Phe His Gly Cys Pro Thr Arg Asp Phe Ser Ala Ala Trp
    50                  55                  60

Val Lys Asp Pro Glu Thr Gly Glu Thr Arg Pro Lys Leu His Arg Val
65                  70                  75                  80

Gly Thr Arg Ser Leu Ser Arg Cys Gln Tyr Val Ala Leu Thr His Pro
                85                  90                  95

Gln Arg Ser Ala Val Leu Val Leu Asp Ile Asp Ile Pro Ser His Gln
            100                 105                 110

Ala Gly Gly Asn Ile Glu His Leu His Pro Gln Val Tyr Ala Thr Leu
        115                 120                 125

Glu Arg Trp Ala Arg Val Glu Lys Ala Pro Ala Trp Ile Gly Val Asn
    130                 135                 140

Pro Leu Ser Gly Lys Cys Gln Leu Ile Trp Cys Ile Asp Pro Val Phe
145                 150                 155                 160

Ala Ala Glu Gly Thr Thr Ser Ser Asn Thr Arg Leu Leu Ala Ala Thr
                165                 170                 175

Thr Glu Glu Met Thr Arg Val Phe Gly Ala Asp Gln Ala Phe Ser His
            180                 185                 190

Arg Leu Ser Arg Trp Pro Leu His Val Ser Asp Asp Pro Thr Ala Tyr
        195                 200                 205

Ser Trp His Cys Gln His Asn Arg Val Asp Ile Leu Asp Glu Leu Met
    210                 215                 220

Glu Val Ala Arg Thr Met Thr Gly Ser Lys Lys Pro Arg Glu His Ala
225                 230                 235                 240

His Gln Glu Phe Ser Ser Gly Arg Ala Arg Ile Glu Ala Ala Arg Lys
                245                 250                 255

Ala Thr Ala Glu Ala Lys Ala Leu Ala Ala Leu Asp Ala Thr Leu Pro
            260                 265                 270

Thr Ala Leu Glu Ala Ser Gly Asp Leu Ile Asp Gly Val Arg Val Leu
        275                 280                 285

Trp Ala Ala Glu Gly Arg Ala Arg Asp Glu Thr Ala Phe Arg His
    290                 295                 300

Ala Leu Thr Val Gly Tyr Gln Leu Lys Ala Ala Gly Glu Arg Leu Lys
305                 310                 315                 320

Asp Ala Lys Ile Ile Asp Ala Tyr Glu Arg Ala Tyr Asn Val Ala Gln
                325                 330                 335

Ala Val Gly Ala Asp Gly Arg Glu Pro Asp Leu Pro Ala Met Arg Asp
            340                 345                 350

Arg Gln Thr Met Ala Arg Arg Val Arg Ala Tyr Val Ala Lys Gly Gln
        355                 360                 365

```
                                                -continued

Pro Thr Val Ser Ala Arg Ser Thr Gln Thr Gln Ser Ser Arg Gly Arg
    370                 375                 380

Lys Ala Leu Ala Thr Met Gly Arg Arg Gly Gln Lys Ala Ala Glu
385                 390                 395                 400

Arg Trp Lys Thr Asp Pro Asn Gly Lys Tyr Ala Gln Glu Asn Arg Gln
                    405                 410                 415

Arg Leu Glu Ala Ala Asn Lys Arg Gln Val Ser Trp Asn Lys Tyr
                420                 425                 430

Ala Ser Thr Asn Ser Gly Tyr Gly Phe Arg His Val Trp Ala Ser Leu
            435                 440                 445

Glu Lys Cys Leu Arg Asp Glu Gln Ile Met Glu Thr Gly Leu Ser
        450                 455                 460

Glu Lys Cys Leu Arg Asp Glu Gln Ile Met Glu Thr Gly Leu Ser
465                 470                 475                 480

Cys Gln Ile Leu Arg Gly Ala His Ala Val Asp Arg
                485                 490

<210> SEQ ID NO 3
<211> LENGTH: 1479
<212> TYPE: DNA
<213> ORGANISM: Corynebacterium thermoaminogenes
<220> FEATURE:
<221> NAME/KEY: CDS
<222> LOCATION: (1)..(1476)
<223> OTHER INFORMATION:

<400> SEQUENCE: 3 atg act cta gcg gat tcg cca gga aca tac aca gca gat gcg tgg aat      48
Met Thr Leu Ala Asp Ser Pro Gly Thr Tyr Thr Ala Asp Ala Trp Asn
1               5                   10                  15 tac tcc act gat ctg ttc gac acc cac cct gag ctg gct tta cgc tcc      96
Tyr Ser Thr Asp Leu Phe Asp Thr His Pro Glu Leu Ala Leu Arg Ser
                20                  25                  30 cgg ggt tgg aat cac cag gac gcc gca gag ttc ctg gcc cac ctg gat     144
Arg Gly Trp Asn His Gln Asp Ala Ala Glu Phe Leu Ala His Leu Asp
            35                  40                  45 cgc agc atg ttt cac ggg tgc ccc acc cgg gat ttc tcc gcg gcc tgg     192
Arg Ser Met Phe His Gly Cys Pro Thr Arg Asp Phe Ser Ala Ala Trp
        50                  55                  60 gtc aaa gac ccg gaa acc gga gaa acc cgc ccc aag ctg cac aga gtt     240
Val Lys Asp Pro Glu Thr Gly Glu Thr Arg Pro Lys Leu His Arg Val
65                  70                  75                  80 ggc acc cgc tca ctt tcc cgg tgc cag tac gtt gcc ctg acc cac ccg     288
Gly Thr Arg Ser Leu Ser Arg Cys Gln Tyr Val Ala Leu Thr His Pro
                85                  90                  95 cag cgc tcc gcg gtg ctg gtc tta gac atc gac atc ccc agc cac cag     336
Gln Arg Ser Ala Val Leu Val Leu Asp Ile Asp Ile Pro Ser His Gln
            100                 105                 110 gcc ggc ggg aac atc gag cac ctt cac ccg cag gtg tac gcc acc ttg     384
Ala Gly Gly Asn Ile Glu His Leu His Pro Gln Val Tyr Ala Thr Leu
        115                 120                 125 gag cgt tgg gca cgg gtg gag aaa gcg ccg gcc tgg atc ggg gtg aac     432
Glu Arg Trp Ala Arg Val Glu Lys Ala Pro Ala Trp Ile Gly Val Asn
    130                 135                 140 ccg ttg tcg gga aag tgc cag ctc atc tgg tgc att gac ccg gtg ttc     480
Pro Leu Ser Gly Lys Cys Gln Leu Ile Trp Cys Ile Asp Pro Val Phe
145                 150                 155                 160 gcc gcc gag ggc acc acc agc tcg aac acc cgc ctg cta gcg gcc acc     528
Ala Ala Glu Gly Thr Thr Ser Ser Asn Thr Arg Leu Leu Ala Ala Thr
                165                 170                 175
```

-continued

| | |
|---|---|
| acc gag gaa atg acc cgt gtg ttc ggc gct gac cag gca ttt tcc cac<br>Thr Glu Glu Met Thr Arg Val Phe Gly Ala Asp Gln Ala Phe Ser His<br>180 185 190 | 576 |
| cgg ctg agc cgg tgg ccg ctg cat gtt ttt gat gat ccg acc gcg tac<br>Arg Leu Ser Arg Trp Pro Leu His Val Phe Asp Asp Pro Thr Ala Tyr<br>195 200 205 | 624 |
| tcc tgg cac tgc cag cac aac cga gtc gat att ctt gat gag ctg atg<br>Ser Trp His Cys Gln His Asn Arg Val Asp Ile Leu Asp Glu Leu Met<br>210 215 220 | 672 |
| gag gta gcc cgc acg atg acc gga tca aaa aag ccg aga aag cac gct<br>Glu Val Ala Arg Thr Met Thr Gly Ser Lys Lys Pro Arg Lys His Ala<br>225 230 235 240 | 720 |
| cac cag gag ttt tcc agc ggt cgg gca cgg atc gaa gcc gcg cgg aaa<br>His Gln Glu Phe Ser Ser Gly Arg Ala Arg Ile Glu Ala Ala Arg Lys<br>245 250 255 | 768 |
| gcc acc gca gag gcc aaa gcg ctt gcc gcc ttg gac gcc acg ctg cct<br>Ala Thr Ala Glu Ala Lys Ala Leu Ala Ala Leu Asp Ala Thr Leu Pro<br>260 265 270 | 816 |
| acg gcg ctg gag gca tca ggc gat ctc att gac ggg gtg cgg gtg ttg<br>Thr Ala Leu Glu Ala Ser Gly Asp Leu Ile Asp Gly Val Arg Val Leu<br>275 280 285 | 864 |
| tgg gca gca gag ggg cgt gca gcc cgt gat gag aca gcg ttt cgc cat<br>Trp Ala Ala Glu Gly Arg Ala Ala Arg Asp Glu Thr Ala Phe Arg His<br>290 295 300 | 912 |
| gcg ttg acc gtg ggt tat cag ctt aaa gcc gca ggt gaa cgc ctg aaa<br>Ala Leu Thr Val Gly Tyr Gln Leu Lys Ala Ala Gly Glu Arg Leu Lys<br>305 310 315 320 | 960 |
| gat gcc aag atc att gat gcg tat gag cgt gcc tac aac gtc gcc cag<br>Asp Ala Lys Ile Ile Asp Ala Tyr Glu Arg Ala Tyr Asn Val Ala Gln<br>325 330 335 | 1008 |
| gcg gtg gga gct gat ggg cgt gaa ccg gat ctg cct gcc atg cgt gat<br>Ala Val Gly Ala Asp Gly Arg Glu Pro Asp Leu Pro Ala Met Arg Asp<br>340 345 350 | 1056 |
| cgt cag acg atg gcc cgc cgt gtg cgc gcc tac gtc gcc aaa ggc cag<br>Arg Gln Thr Met Ala Arg Arg Val Arg Ala Tyr Val Ala Lys Gly Gln<br>355 360 365 | 1104 |
| ccc acg gtc agc gcc agg agc aca cag acc cag agc agt cgg ggc cgg<br>Pro Thr Val Ser Ala Arg Ser Thr Gln Thr Gln Ser Ser Arg Gly Arg<br>370 375 380 | 1152 |
| aaa gcc ctg gcc acc atg ggc cgc aga ggc ggg caa aaa gcc gct gaa<br>Lys Ala Leu Ala Thr Met Gly Arg Arg Gly Gly Gln Lys Ala Ala Glu<br>385 390 395 400 | 1200 |
| cgc tgg aaa acc gat cct aac ggc aaa tac gcc caa gaa aac cgc caa<br>Arg Trp Lys Thr Asp Pro Asn Gly Lys Tyr Ala Gln Glu Asn Arg Gln<br>405 410 415 | 1248 |
| cga ctc gaa gct gca aac aag cga cgt caa gtc agc tgg aac aaa tac<br>Arg Leu Glu Ala Ala Asn Lys Arg Arg Gln Val Ser Trp Asn Lys Tyr<br>420 425 430 | 1296 |
| gcg agc acg aat tct ggc tac ggt ttc cga cac gta tgg gcc agc ttg<br>Ala Ser Thr Asn Ser Gly Tyr Gly Phe Arg His Val Trp Ala Ser Leu<br>435 440 445 | 1344 |
| gaa aaa tgc cta cgc gac gag caa atc atg gaa gaa aca ggg ctt tca<br>Glu Lys Cys Leu Arg Asp Glu Gln Ile Met Glu Glu Thr Gly Leu Ser<br>450 455 460 | 1392 |
| cga gct acc gtg acg cgc cat tgg gtg cac tgc gag agg ctg gcc tgc<br>Arg Ala Thr Val Thr Arg His Trp Val His Cys Glu Arg Leu Ala Cys<br>465 470 475 480 | 1440 |
| tgc caa atc ctt agg ggg gct cac gcc gta cac aga taa<br>Cys Gln Ile Leu Arg Gly Ala His Ala Val His Arg | 1479 |

485        490

<210> SEQ ID NO 4
<211> LENGTH: 492
<212> TYPE: PRT
<213> ORGANISM: Corynebacterium thermoaminogenes

<400> SEQUENCE: 4

Met Thr Leu Ala Asp Ser Pro Gly Thr Tyr Thr Ala Asp Ala Trp Asn
1               5                   10                  15

Tyr Ser Thr Asp Leu Phe Asp Thr His Pro Glu Leu Ala Leu Arg Ser
            20                  25                  30

Arg Gly Trp Asn His Gln Asp Ala Ala Glu Phe Leu Ala His Leu Asp
        35                  40                  45

Arg Ser Met Phe His Gly Cys Pro Thr Arg Asp Phe Ser Ala Ala Trp
    50                  55                  60

Val Lys Asp Pro Glu Thr Gly Glu Thr Arg Pro Lys Leu His Arg Val
65                  70                  75                  80

Gly Thr Arg Ser Leu Ser Arg Cys Gln Tyr Val Ala Leu Thr His Pro
                85                  90                  95

Gln Arg Ser Ala Val Leu Val Leu Asp Ile Asp Ile Pro Ser His Gln
            100                 105                 110

Ala Gly Gly Asn Ile Glu His Leu His Pro Gln Val Tyr Ala Thr Leu
        115                 120                 125

Glu Arg Trp Ala Arg Val Glu Lys Ala Pro Ala Trp Ile Gly Val Asn
    130                 135                 140

Pro Leu Ser Gly Lys Cys Gln Leu Ile Trp Cys Ile Asp Pro Val Phe
145                 150                 155                 160

Ala Ala Glu Gly Thr Thr Ser Ser Asn Thr Arg Leu Leu Ala Ala Thr
                165                 170                 175

Thr Glu Glu Met Thr Arg Val Phe Gly Ala Asp Gln Ala Phe Ser His
            180                 185                 190

Arg Leu Ser Arg Trp Pro Leu His Val Phe Asp Asp Pro Thr Ala Tyr
        195                 200                 205

Ser Trp His Cys Gln His Asn Arg Val Asp Ile Leu Asp Glu Leu Met
    210                 215                 220

Glu Val Ala Arg Thr Met Thr Gly Ser Lys Lys Pro Arg Lys His Ala
225                 230                 235                 240

His Gln Glu Phe Ser Ser Gly Arg Ala Arg Ile Glu Ala Ala Arg Lys
                245                 250                 255

Ala Thr Ala Glu Ala Lys Ala Leu Ala Ala Leu Asp Ala Thr Leu Pro
            260                 265                 270

Thr Ala Leu Glu Ala Ser Gly Asp Leu Ile Asp Gly Val Arg Val Leu
        275                 280                 285

Trp Ala Ala Glu Gly Arg Ala Arg Asp Glu Thr Ala Phe Arg His
    290                 295                 300

Ala Leu Thr Val Gly Tyr Gln Leu Lys Ala Ala Gly Glu Arg Leu Lys
305                 310                 315                 320

Asp Ala Lys Ile Ile Asp Ala Tyr Glu Arg Ala Tyr Asn Val Ala Gln
                325                 330                 335

Ala Val Gly Ala Asp Gly Arg Glu Pro Asp Leu Pro Ala Met Arg Asp
            340                 345                 350

Arg Gln Thr Met Ala Arg Arg Val Arg Ala Tyr Val Ala Lys Gly Gln
        355                 360                 365

-continued

```
Pro Thr Val Ser Ala Arg Ser Thr Gln Thr Gln Ser Ser Arg Gly Arg
    370                 375                 380

Lys Ala Leu Ala Thr Met Gly Arg Arg Gly Gly Gln Lys Ala Ala Glu
385                 390                 395                 400

Arg Trp Lys Thr Asp Pro Asn Gly Lys Tyr Ala Gln Glu Asn Arg Gln
                405                 410                 415

Arg Leu Glu Ala Ala Asn Lys Arg Arg Gln Val Ser Trp Asn Lys Tyr
            420                 425                 430

Ala Ser Thr Asn Ser Gly Tyr Gly Phe Arg His Val Trp Ala Ser Leu
        435                 440                 445

Glu Lys Cys Leu Arg Asp Glu Gln Ile Met Glu Thr Gly Leu Ser
    450                 455                 460

Arg Ala Thr Val Thr Arg His Trp Val His Cys Glu Arg Leu Ala Cys
465                 470                 475                 480

Cys Gln Ile Leu Arg Gly Ala His Ala Val His Arg
                485                 490
```

<210> SEQ ID NO 5
<211> LENGTH: 1479
<212> TYPE: DNA
<213> ORGANISM: Corynebacterium thermoaminogenes
<220> FEATURE:
<221> NAME/KEY: CDS
<222> LOCATION: (1)..(1476)
<223> OTHER INFORMATION:

<400> SEQUENCE: 5

```
atg act cta gcg gat tcg cca gga aca tac aca gca gat gcg tgg aat     48
Met Thr Leu Ala Asp Ser Pro Gly Thr Tyr Thr Ala Asp Ala Trp Asn
1               5                   10                  15 tac tcc act gat ctg ttc gac acc cac cct gag ctg gct tta cgc tcc     96
Tyr Ser Thr Asp Leu Phe Asp Thr His Pro Glu Leu Ala Leu Arg Ser
                20                  25                  30 cgg ggt tgg aat cac cag gac gcc gcc gag ttc ctg gcc cac ctg gat    144
Arg Gly Trp Asn His Gln Asp Ala Ala Glu Phe Leu Ala His Leu Asp
            35                  40                  45 cgc agc atg ttt cac ggg tgc ccc acc cgg gat ttc tcc gcg gcc tgg    192
Arg Ser Met Phe His Gly Cys Pro Thr Arg Asp Phe Ser Ala Ala Trp
        50                  55                  60 gtc aaa gac ccg gaa acc gga gaa acc cgc ccc aag ctg cac aga gtt    240
Val Lys Asp Pro Glu Thr Gly Glu Thr Arg Pro Lys Leu His Arg Val
65                  70                  75                  80 ggc acc cgc tca ctt tcc cgg tgc cag tac gtt gcc ctg acc cac ccg    288
Gly Thr Arg Ser Leu Ser Arg Cys Gln Tyr Val Ala Leu Thr His Pro
                85                  90                  95 cag cgc tcc gcg gtg ctg gtc tta gac atc gac atc ccc agc cac cag    336
Gln Arg Ser Ala Val Leu Val Leu Asp Ile Asp Ile Pro Ser His Gln
                100                 105                 110 gcc ggc ggg aac atc gag cac ctt cac ccg cag gta tac gcc acc ttg    384
Ala Gly Gly Asn Ile Glu His Leu His Pro Gln Val Tyr Ala Thr Leu
            115                 120                 125 gag cgt tgg gca cgg gtg gag aaa gcg ccg gcc tgg atc ggg gtg aac    432
Glu Arg Trp Ala Arg Val Glu Lys Ala Pro Ala Trp Ile Gly Val Asn
        130                 135                 140 ccg ttg tcg gga aag tgc cag ctc atc tgg tgc att gac ccg gtg ttc    480
Pro Leu Ser Gly Lys Cys Gln Leu Ile Trp Cys Ile Asp Pro Val Phe
145                 150                 155                 160 gcc gcc gag ggc acc acc agc tcg aac acc cgc ctg cta gcg gcc acc    528
Ala Ala Glu Gly Thr Thr Ser Ser Asn Thr Arg Leu Leu Ala Ala Thr
                165                 170                 175
```

```
acc gag gaa atg acc cgt gtg ttc ggc gct gac cag gca ttt tcc cac      576
Thr Glu Glu Met Thr Arg Val Phe Gly Ala Asp Gln Ala Phe Ser His
            180                 185                 190 cgg ctg agc cgg tgg ccg ctg cat gtt tct gat gat ccg acc gcg tac      624
Arg Leu Ser Arg Trp Pro Leu His Val Ser Asp Asp Pro Thr Ala Tyr
        195                 200                 205 tcc tgg cac tgc cag cac aac cga gtc gat acg ctt gat gag ctg atg      672
Ser Trp His Cys Gln His Asn Arg Val Asp Thr Leu Asp Glu Leu Met
    210                 215                 220 gag gta gcc cgc acg atg acc gga tca aaa aag ccg aga aag cac gct      720
Glu Val Ala Arg Thr Met Thr Gly Ser Lys Lys Pro Arg Lys His Ala
225                 230                 235                 240 cac cag gag ttt tcc agc ggt cgg gca cgg atc gaa gcc gcg cgg aaa      768
His Gln Glu Phe Ser Ser Gly Arg Ala Arg Ile Glu Ala Ala Arg Lys
                245                 250                 255 gcc acc gca gag gcc aaa gcg ctt gcc gcc ttg gac gcc acg ctg cct      816
Ala Thr Ala Glu Ala Lys Ala Leu Ala Ala Leu Asp Ala Thr Leu Pro
            260                 265                 270 acg gcg ctg gag gca tca ggc gat ctc att gac ggg gtg cgg gtg ttg      864
Thr Ala Leu Glu Ala Ser Gly Asp Leu Ile Asp Gly Val Arg Val Leu
        275                 280                 285 tgg gca gca gag ggg cgt gca gcc cgt gat gag aca gcg ttt cgc cat      912
Trp Ala Ala Glu Gly Arg Ala Ala Arg Asp Glu Thr Ala Phe Arg His
    290                 295                 300 gcg ttg acc gtg ggt tat cag ctt aaa gcc gca ggt gaa cgc ctg aaa      960
Ala Leu Thr Val Gly Tyr Gln Leu Lys Ala Ala Gly Glu Arg Leu Lys
305                 310                 315                 320 gat gcc aag atc att gat gcg tat gag cgt gcc tac aac gtc gcc cag     1008
Asp Ala Lys Ile Ile Asp Ala Tyr Glu Arg Ala Tyr Asn Val Ala Gln
                325                 330                 335 gcg gtg gga gct gat ggg cgt gaa ccg gat ctg cct gcc atg cgt gat     1056
Ala Val Gly Ala Asp Gly Arg Glu Pro Asp Leu Pro Ala Met Arg Asp
            340                 345                 350 cgt cag acg atg gcc cgc cgt gtg cgc gcc tac gtc gcc aaa ggc cag     1104
Arg Gln Thr Met Ala Arg Arg Val Arg Ala Tyr Val Ala Lys Gly Gln
        355                 360                 365 ccc acg gtc agc gcc agg agc aca cag acc cag agc agt cgg ggc cgg     1152
Pro Thr Val Ser Ala Arg Ser Thr Gln Thr Gln Ser Ser Arg Gly Arg
    370                 375                 380 aaa gcc ctg gcc acc atg ggc cgc aga ggc ggg caa aaa gcc gct gaa     1200
Lys Ala Leu Ala Thr Met Gly Arg Arg Gly Gly Gln Lys Ala Ala Glu
385                 390                 395                 400 cgc tgg aaa acc gat cct aac ggc aaa tac gcc caa gaa aac cgc caa     1248
Arg Trp Lys Thr Asp Pro Asn Gly Lys Tyr Ala Gln Glu Asn Arg Gln
                405                 410                 415 cga ctc gaa gct gca aac aag cga cgt caa gtc agc tgg aac aaa tac     1296
Arg Leu Glu Ala Ala Asn Lys Arg Arg Gln Val Ser Trp Asn Lys Tyr
            420                 425                 430 gcg agc acg aat tct ggc tac ggt ttc cga cac gta tgg gcc agc ttg     1344
Ala Ser Thr Asn Ser Gly Tyr Gly Phe Arg His Val Trp Ala Ser Leu
        435                 440                 445 gaa aaa tgc cta cgc gac gag caa atc atg gaa gaa aca ggg ctt tca     1392
Glu Lys Cys Leu Arg Asp Glu Gln Ile Met Glu Glu Thr Gly Leu Ser
    450                 455                 460 cga gct acc gtg acg cgc cat tgg gtg cac tgc gag agg ctg gcc tgc     1440
Arg Ala Thr Val Thr Arg His Trp Val His Cys Glu Arg Leu Ala Cys
465                 470                 475                 480 tgc caa atc ctt agg ggg gct cac gcc gta cac aga taa                 1479
Cys Gln Ile Leu Arg Gly Ala His Ala Val His Arg
```

485 490

<210> SEQ ID NO 6
<211> LENGTH: 492
<212> TYPE: PRT
<213> ORGANISM: Corynebacterium thermoaminogenes

<400> SEQUENCE: 6

Met Thr Leu Ala Asp Ser Pro Gly Thr Tyr Thr Ala Asp Ala Trp Asn
1               5                   10                  15

Tyr Ser Thr Asp Leu Phe Asp Thr His Pro Glu Leu Ala Leu Arg Ser
            20                  25                  30

Arg Gly Trp Asn His Gln Asp Ala Ala Glu Phe Leu Ala His Leu Asp
        35                  40                  45

Arg Ser Met Phe His Gly Cys Pro Thr Arg Asp Phe Ser Ala Ala Trp
    50                  55                  60

Val Lys Asp Pro Glu Thr Gly Glu Thr Arg Pro Lys Leu His Arg Val
65                  70                  75                  80

Gly Thr Arg Ser Leu Ser Arg Cys Gln Tyr Val Ala Leu Thr His Pro
                85                  90                  95

Gln Arg Ser Ala Val Leu Val Leu Asp Ile Asp Ile Pro Ser His Gln
            100                 105                 110

Ala Gly Gly Asn Ile Glu His Leu His Pro Gln Val Tyr Ala Thr Leu
        115                 120                 125

Glu Arg Trp Ala Arg Val Glu Lys Ala Pro Ala Trp Ile Gly Val Asn
    130                 135                 140

Pro Leu Ser Gly Lys Cys Gln Leu Ile Trp Cys Ile Asp Pro Val Phe
145                 150                 155                 160

Ala Ala Glu Gly Thr Thr Ser Ser Asn Thr Arg Leu Leu Ala Ala Thr
                165                 170                 175

Thr Glu Glu Met Thr Arg Val Phe Gly Ala Asp Gln Ala Phe Ser His
            180                 185                 190

Arg Leu Ser Arg Trp Pro Leu His Val Ser Asp Asp Pro Thr Ala Tyr
        195                 200                 205

Ser Trp His Cys Gln His Asn Arg Val Asp Thr Leu Asp Glu Leu Met
    210                 215                 220

Glu Val Ala Arg Thr Met Thr Gly Ser Lys Lys Pro Arg Lys His Ala
225                 230                 235                 240

His Gln Glu Phe Ser Ser Gly Arg Ala Arg Ile Glu Ala Ala Arg Lys
                245                 250                 255

Ala Thr Ala Glu Ala Lys Ala Leu Ala Ala Leu Asp Ala Thr Leu Pro
            260                 265                 270

Thr Ala Leu Glu Ala Ser Gly Asp Leu Ile Asp Gly Val Arg Val Leu
        275                 280                 285

Trp Ala Ala Glu Gly Arg Ala Arg Asp Glu Thr Ala Phe Arg His
    290                 295                 300

Ala Leu Thr Val Gly Tyr Gln Leu Lys Ala Ala Gly Glu Arg Leu Lys
305                 310                 315                 320

Asp Ala Lys Ile Ile Asp Ala Tyr Glu Arg Ala Tyr Asn Val Ala Gln
                325                 330                 335

Ala Val Gly Ala Asp Gly Arg Glu Pro Asp Leu Pro Ala Met Arg Asp
            340                 345                 350

Arg Gln Thr Met Ala Arg Arg Val Arg Ala Tyr Val Ala Lys Gly Gln
        355                 360                 365

-continued

```
Pro Thr Val Ser Ala Arg Ser Thr Gln Thr Gln Ser Ser Arg Gly Arg
    370                 375                 380

Lys Ala Leu Ala Thr Met Gly Arg Arg Gly Gly Gln Lys Ala Ala Glu
385                 390                 395                 400

Arg Trp Lys Thr Asp Pro Asn Gly Lys Tyr Ala Gln Glu Asn Arg Gln
                405                 410                 415

Arg Leu Glu Ala Ala Asn Lys Arg Arg Gln Val Ser Trp Asn Lys Tyr
            420                 425                 430

Ala Ser Thr Asn Ser Gly Tyr Gly Phe Arg His Val Trp Ala Ser Leu
        435                 440                 445

Glu Lys Cys Leu Arg Asp Glu Gln Ile Met Glu Thr Gly Leu Ser
    450                 455                 460

Arg Ala Thr Val Thr Arg His Trp Val His Cys Glu Arg Leu Ala Cys
465                 470                 475                 480

Cys Gln Ile Leu Arg Gly Ala His Ala Val His Arg
                485                 490
```

<210> SEQ ID NO 7
<211> LENGTH: 1377
<212> TYPE: DNA
<213> ORGANISM: Corynebacterium thermoaminogenes
<220> FEATURE:
<221> NAME/KEY: CDS
<222> LOCATION: (1)..(1374)
<223> OTHER INFORMATION:

<400> SEQUENCE: 7

```
atg act cta gcg gat tcg cca gga aca tac aca gca gat gcg tgg aat        48
Met Thr Leu Ala Asp Ser Pro Gly Thr Tyr Thr Ala Asp Ala Trp Asn
1               5                   10                  15 tac tcc aca gat ctg ttc gac acc cac cct gag ctg gct tta cgc tcc        96
Tyr Ser Thr Asp Leu Phe Asp Thr His Pro Glu Leu Ala Leu Arg Ser
                20                  25                  30 cgg ggt tgg aat cac cag gac gcc gcc gag ttc ctg gcc cac ctg gat       144
Arg Gly Trp Asn His Gln Asp Ala Ala Glu Phe Leu Ala His Leu Asp
            35                  40                  45 cgc agc atg ttt cac ggg tgc ccc acc cgg gat ttc tcc gcg gcc tgg       192
Arg Ser Met Phe His Gly Cys Pro Thr Arg Asp Phe Ser Ala Ala Trp
        50                  55                  60 gtc aaa gac ccg gag acc gga gaa acc cgc cct aag ctg cac aga gtc       240
Val Lys Asp Pro Glu Thr Gly Glu Thr Arg Pro Lys Leu His Arg Val
65                  70                  75                  80 ggc acc cgg tcg ctt tcc cga tgc cag tac gtc gcg ctg acc cac ccg       288
Gly Thr Arg Ser Leu Ser Arg Cys Gln Tyr Val Ala Leu Thr His Pro
                85                  90                  95 cag cgc tcc gcg gtg ctg gtc tta gac atc gac atc ccc agc cac cag       336
Gln Arg Ser Ala Val Leu Val Leu Asp Ile Asp Ile Pro Ser His Gln
            100                 105                 110 gcc ggc ggg aac atc gag cac ctt cac ccg cag gtc tac gcc acc ttg       384
Ala Gly Gly Asn Ile Glu His Leu His Pro Gln Val Tyr Ala Thr Leu
        115                 120                 125 gag cgc tgg gca cgg gtg gag aaa gcg ccg gcc tgg atc ggg gtg aac       432
Glu Arg Trp Ala Arg Val Glu Lys Ala Pro Ala Trp Ile Gly Val Asn
    130                 135                 140 ccg ttg tca gga aag tgc cag ctc atc tgg tgc att gac ccg gtg ttc       480
Pro Leu Ser Gly Lys Cys Gln Leu Ile Trp Cys Ile Asp Pro Val Phe
145                 150                 155                 160 gcc gcc gag ggc acc acc agc ccg aac acc cgc ctg cta gcg gcc acc       528
Ala Ala Glu Gly Thr Thr Ser Pro Asn Thr Arg Leu Leu Ala Ala Thr
                165                 170                 175
```

```
acc gag gaa atg acc cgt atg ttc ggc gct gac cag gca ttt tcc cac      576
Thr Glu Glu Met Thr Arg Met Phe Gly Ala Asp Gln Ala Phe Ser His
            180                 185                 190 cgg ctg agc cgg tgg ccg ctg cat gta tct gat gat ccg acc gcg tac      624
Arg Leu Ser Arg Trp Pro Leu His Val Ser Asp Asp Pro Thr Ala Tyr
        195                 200                 205 tcc tgg cac tgc cag cac aac cga gtc gat acg ctt gct gag ctg atg      672
Ser Trp His Cys Gln His Asn Arg Val Asp Thr Leu Ala Glu Leu Met
    210                 215                 220 gag gta gcc cgc acg atg acc gga tca aaa aag cca gat agc act gct      720
Glu Val Ala Arg Thr Met Thr Gly Ser Lys Lys Pro Asp Ser Thr Ala
225                 230                 235                 240 cac cag gag ttt tcc agc ggt cgg gca cgg atc gaa gcc gcg agg aaa      768
His Gln Glu Phe Ser Ser Gly Arg Ala Arg Ile Glu Ala Ala Arg Lys
                245                 250                 255 gcc acc gca gaa gcc aaa gcg ctt gct gcc tta gac gcc acg ctg cct      816
Ala Thr Ala Glu Ala Lys Ala Leu Ala Ala Leu Asp Ala Thr Leu Pro
            260                 265                 270 acg gcg ctg gag gca tca ggc gat ctc att gac ggg gtg cgg gtg ctg      864
Thr Ala Leu Glu Ala Ser Gly Asp Leu Ile Asp Gly Val Arg Val Leu
        275                 280                 285 tgg gca gca gag ggg cgt gca gcc cgt gat gag acg gcg ttt cgc cat      912
Trp Ala Ala Glu Gly Arg Ala Ala Arg Asp Glu Thr Ala Phe Arg His
    290                 295                 300 gcg ttg acc gtg ggg tat cag ctt aaa gcc gca ggt gaa cgc ctg aaa      960
Ala Leu Thr Val Gly Tyr Gln Leu Lys Ala Ala Gly Glu Arg Leu Lys
305                 310                 315                 320 gac acc aag atc att gat gcg tat gag cgt gcc tac aac gtc gcc cag     1008
Asp Thr Lys Ile Ile Asp Ala Tyr Glu Arg Ala Tyr Asn Val Ala Gln
                325                 330                 335 gcg gtg ggg gct gat ggg cgt gag ccg gat ctg cct gcc atg cgt gat     1056
Ala Val Gly Ala Asp Gly Arg Glu Pro Asp Leu Pro Ala Met Arg Asp
            340                 345                 350 cgt cag acg ttg gcc cgt cgt gtg cgc gcc tac gtc gct aaa ggc cag     1104
Arg Gln Thr Leu Ala Arg Arg Val Arg Ala Tyr Val Ala Lys Gly Gln
        355                 360                 365 ccc acg gtg agc gcc agg agc aca cag acc cag agc agc cgg ggc agg     1152
Pro Thr Val Ser Ala Arg Ser Thr Gln Thr Gln Ser Ser Arg Gly Arg
    370                 375                 380 aaa gcc ctg gcc acc atg gga cgc aga ggc gca gcc acc tcg aat gca     1200
Lys Ala Leu Ala Thr Met Gly Arg Arg Gly Ala Ala Thr Ser Asn Ala
385                 390                 395                 400 cgc agg tgg gca gac cca gaa agc gat tac gcc cgc caa act cgg gag     1248
Arg Arg Trp Ala Asp Pro Glu Ser Asp Tyr Ala Arg Gln Thr Arg Glu
                405                 410                 415 cgt tta gcc cga gca atg agc ttc gta cat tca gca cag acg aga aca     1296
Arg Leu Ala Arg Ala Met Ser Phe Val His Ser Ala Gln Thr Arg Thr
            420                 425                 430 agg gcc gga tcc tgg cct acg ttt ccg agt gca agc gcc acg gtt acg     1344
Arg Ala Gly Ser Trp Pro Thr Phe Pro Ser Ala Ser Ala Thr Val Thr
        435                 440                 445 acc cca cga gca aag aag tcg caa cgg agc tag                         1377
Thr Pro Arg Ala Lys Lys Ser Gln Arg Ser
    450                 455

<210> SEQ ID NO 8
<211> LENGTH: 458
<212> TYPE: PRT
<213> ORGANISM: Corynebacterium thermoaminogenes
```

-continued

<400> SEQUENCE: 8

```
Met Thr Leu Ala Asp Ser Pro Gly Thr Tyr Thr Ala Asp Ala Trp Asn
1               5                   10                  15

Tyr Ser Thr Asp Leu Phe Asp Thr His Pro Glu Leu Ala Leu Arg Ser
            20                  25                  30

Arg Gly Trp Asn His Gln Asp Ala Ala Glu Phe Leu Ala His Leu Asp
        35                  40                  45

Arg Ser Met Phe His Gly Cys Pro Thr Arg Asp Phe Ser Ala Ala Trp
    50                  55                  60

Val Lys Asp Pro Glu Thr Gly Glu Thr Arg Pro Lys Leu His Arg Val
65                  70                  75                  80

Gly Thr Arg Ser Leu Ser Arg Cys Gln Tyr Val Ala Leu Thr His Pro
                85                  90                  95

Gln Arg Ser Ala Val Leu Val Leu Asp Ile Asp Ile Pro Ser His Gln
            100                 105                 110

Ala Gly Gly Asn Ile Glu His Leu His Pro Gln Val Tyr Ala Thr Leu
        115                 120                 125

Glu Arg Trp Ala Arg Val Glu Lys Ala Pro Ala Trp Ile Gly Val Asn
    130                 135                 140

Pro Leu Ser Gly Lys Cys Gln Leu Ile Trp Cys Ile Asp Pro Val Phe
145                 150                 155                 160

Ala Ala Glu Gly Thr Thr Ser Pro Asn Thr Arg Leu Leu Ala Ala Thr
                165                 170                 175

Thr Glu Glu Met Thr Arg Met Phe Gly Ala Asp Gln Ala Phe Ser His
            180                 185                 190

Arg Leu Ser Arg Trp Pro Leu His Val Ser Asp Asp Pro Thr Ala Tyr
        195                 200                 205

Ser Trp His Cys Gln His Asn Arg Val Asp Thr Leu Ala Glu Leu Met
    210                 215                 220

Glu Val Ala Arg Thr Met Thr Gly Ser Lys Lys Pro Asp Ser Thr Ala
225                 230                 235                 240

His Gln Glu Phe Ser Ser Gly Arg Ala Arg Ile Glu Ala Ala Arg Lys
                245                 250                 255

Ala Thr Ala Glu Ala Lys Ala Leu Ala Ala Leu Asp Ala Thr Leu Pro
            260                 265                 270

Thr Ala Leu Glu Ala Ser Gly Asp Leu Ile Asp Gly Val Arg Val Leu
        275                 280                 285

Trp Ala Ala Glu Gly Arg Ala Ala Arg Asp Glu Thr Ala Phe Arg His
    290                 295                 300

Ala Leu Thr Val Gly Tyr Gln Leu Lys Ala Ala Gly Glu Arg Leu Lys
305                 310                 315                 320

Asp Thr Lys Ile Ile Asp Ala Tyr Glu Arg Ala Tyr Asn Val Ala Gln
                325                 330                 335

Ala Val Gly Ala Asp Gly Arg Glu Pro Asp Leu Pro Ala Met Arg Asp
            340                 345                 350

Arg Gln Thr Leu Ala Arg Val Arg Ala Tyr Val Ala Lys Gly Gln
        355                 360                 365

Pro Thr Val Ser Ala Arg Ser Thr Gln Thr Gln Ser Ser Arg Gly Arg
370                 375                 380

Lys Ala Leu Ala Thr Met Gly Arg Arg Gly Ala Ala Thr Ser Asn Ala
385                 390                 395                 400

Arg Arg Trp Ala Asp Pro Glu Ser Asp Tyr Ala Arg Gln Thr Arg Glu
                405                 410                 415
```

```
Arg Leu Ala Arg Ala Met Ser Phe Val His Ser Ala Gln Thr Arg Thr
            420                 425                 430
Arg Ala Gly Ser Trp Pro Thr Phe Pro Ser Ala Ser Ala Thr Val Thr
            435                 440                 445
Thr Pro Arg Ala Lys Lys Ser Gln Arg Ser
        450                 455

<210> SEQ ID NO 9
<211> LENGTH: 4369
<212> TYPE: DNA
<213> ORGANISM: Corynebacterium thermoaminogenes
<220> FEATURE:
<221> NAME/KEY: CDS
<222> LOCATION: (1)..(1476)
<223> OTHER INFORMATION:

<400> SEQUENCE: 9 atg act cta gcg gat tcg cca gga aca tac aca gca gat gcg tgg aat        48
Met Thr Leu Ala Asp Ser Pro Gly Thr Tyr Thr Ala Asp Ala Trp Asn
1               5                  10                  15 tac tcc act gat ctg ttc gac acc cac cct gag ctg gct tta cgc tcc        96
Tyr Ser Thr Asp Leu Phe Asp Thr His Pro Glu Leu Ala Leu Arg Ser
            20                  25                  30 cgg ggt tgg aat cac cag gac gcc gca gag ttc ctg gcc cac ctg gat       144
Arg Gly Trp Asn His Gln Asp Ala Ala Glu Phe Leu Ala His Leu Asp
        35                  40                  45 cgc agc atg ttt cac ggg tgc ccc acc cgg gat ttc tcc gcg gcc tgg       192
Arg Ser Met Phe His Gly Cys Pro Thr Arg Asp Phe Ser Ala Ala Trp
    50                  55                  60 gtc aaa gac ccg gaa acc gga gaa acc cgc ccc aag ctg cac aga gtt       240
Val Lys Asp Pro Glu Thr Gly Glu Thr Arg Pro Lys Leu His Arg Val
65                  70                  75                  80 ggc acc cgc tca ctt tcc cgg tgc cag tac gtt gcc ctg acc cac ccg       288
Gly Thr Arg Ser Leu Ser Arg Cys Gln Tyr Val Ala Leu Thr His Pro
                85                  90                  95 cag cgc tcc gcg gtg ctg gtc tta gac atc gac atc ccc agc cac cag       336
Gln Arg Ser Ala Val Leu Val Leu Asp Ile Asp Ile Pro Ser His Gln
            100                 105                 110 gcc ggc ggg aac atc gag cac ctt cac ccg cag gtg tac gcc acc ttg       384
Ala Gly Gly Asn Ile Glu His Leu His Pro Gln Val Tyr Ala Thr Leu
        115                 120                 125 gag cgt tgg gca cgg gtg gag aaa gcg ccg gcc tgg atc ggg gtg aac       432
Glu Arg Trp Ala Arg Val Glu Lys Ala Pro Ala Trp Ile Gly Val Asn
    130                 135                 140 ccg ttg tcg gga aag tgc cag ctc atc tgg tgc att gac ccg gtg ttc       480
Pro Leu Ser Gly Lys Cys Gln Leu Ile Trp Cys Ile Asp Pro Val Phe
145                 150                 155                 160 gcc gcc gag ggc acc acc agc tcg aac acc cgc ctg cta gcg gcc acc       528
Ala Ala Glu Gly Thr Thr Ser Ser Asn Thr Arg Leu Leu Ala Ala Thr
                165                 170                 175 acc gag gaa atg acc cgt gtg ttc ggc gct gac cag gca ttt tcc cac       576
Thr Glu Glu Met Thr Arg Val Phe Gly Ala Asp Gln Ala Phe Ser His
            180                 185                 190 cgg ctg agc cgg tgg ccg ctg cat gtt ttt gat gat ccg acc gcg tac       624
Arg Leu Ser Arg Trp Pro Leu His Val Phe Asp Asp Pro Thr Ala Tyr
        195                 200                 205 tcc tgg cac tgc cag cac aac cga gtc gat att ctt gat gag ctg atg       672
Ser Trp His Cys Gln His Asn Arg Val Asp Ile Leu Asp Glu Leu Met
    210                 215                 220 gag gta gcc cgc acg atg acc gga tca aaa aag ccg aga aag cac gct       720
```

```
Glu Val Ala Arg Thr Met Thr Gly Ser Lys Lys Pro Arg Lys His Ala
225                 230                 235                 240 cac cag gag ttt tcc agc ggt cgg gca cgg atc gaa gcc gcg cgg aaa         768
His Gln Glu Phe Ser Ser Gly Arg Ala Arg Ile Glu Ala Ala Arg Lys
                245                 250                 255 gcc acc gca gag gcc aaa gcg ctt gcc gcc ttg gac gcc acg ctg cct         816
Ala Thr Ala Glu Ala Lys Ala Leu Ala Ala Leu Asp Ala Thr Leu Pro
            260                 265                 270 acg gcg ctg gag gca tca ggc gat ctc att gac ggg gtg cgg gtg ttg         864
Thr Ala Leu Glu Ala Ser Gly Asp Leu Ile Asp Gly Val Arg Val Leu
        275                 280                 285 tgg gca gca gag ggg cgt gca gcc cgt gat gag aca gcg ttt cgc cat         912
Trp Ala Ala Glu Gly Arg Ala Ala Arg Asp Glu Thr Ala Phe Arg His
    290                 295                 300 gcg ttg acc gtg ggt tat cag ctt aaa gcc gca ggt gaa cgc ctg aaa         960
Ala Leu Thr Val Gly Tyr Gln Leu Lys Ala Ala Gly Glu Arg Leu Lys
305                 310                 315                 320 gat gcc aag atc att gat gcg tat gag cgt gcc tac aac gtc gcc cag        1008
Asp Ala Lys Ile Ile Asp Ala Tyr Glu Arg Ala Tyr Asn Val Ala Gln
                325                 330                 335 gcg gtg gga gct gat ggg cgt gaa ccg gat ctg cct gcc atg cgt gat        1056
Ala Val Gly Ala Asp Gly Arg Glu Pro Asp Leu Pro Ala Met Arg Asp
            340                 345                 350 cgt cag acg atg gcc cgc cgt gtg cgc gcc tac gtc gcc aaa ggc cag        1104
Arg Gln Thr Met Ala Arg Arg Val Arg Ala Tyr Val Ala Lys Gly Gln
        355                 360                 365 ccc acg gtc agc gcc agg agc aca cag acc cag agc agt cgg ggc cgg        1152
Pro Thr Val Ser Ala Arg Ser Thr Gln Thr Gln Ser Ser Arg Gly Arg
    370                 375                 380 aaa gcc ctg gcc acc atg ggc cgc aga ggc ggg caa aaa gcc gct gaa        1200
Lys Ala Leu Ala Thr Met Gly Arg Arg Gly Gly Gln Lys Ala Ala Glu
385                 390                 395                 400 cgc tgg aaa acc gat cct aac ggc aaa tac gcc caa gaa aac cgc caa        1248
Arg Trp Lys Thr Asp Pro Asn Gly Lys Tyr Ala Gln Glu Asn Arg Gln
                405                 410                 415 cga ctc gaa gct gca aac aag cga cgt caa gtc agc tgg aac aaa tac        1296
Arg Leu Glu Ala Ala Asn Lys Arg Arg Gln Val Ser Trp Asn Lys Tyr
            420                 425                 430 gcg agc acg aat tct ggc tac ggt ttc cga cac gta tgg gcc agc ttg        1344
Ala Ser Thr Asn Ser Gly Tyr Gly Phe Arg His Val Trp Ala Ser Leu
        435                 440                 445 gaa aaa tgc cta cgc gac gag caa atc atg gaa gaa aca ggg ctt tca        1392
Glu Lys Cys Leu Arg Asp Glu Gln Ile Met Glu Glu Thr Gly Leu Ser
    450                 455                 460 cga gct acc gtg acg cgc cat tgg gtg cac tgc gag agg ctg gcc tgc        1440
Arg Ala Thr Val Thr Arg His Trp Val His Cys Glu Arg Leu Ala Cys
465                 470                 475                 480 tgc caa atc ctt agg ggg gct cac gcc gta cac aga taacggttcc             1486
Cys Gln Ile Leu Arg Gly Ala His Ala Val His Arg
                485                 490 caccccgtag gggtagcgct tggtccctga agctccggct cccatccctc ctcagcactc      1546
cctccccgag gggggggctc acgccgtaga cagataacgg ttcccacccc gtagggggtag      1606 cgcttggtcc ctgaagctct cacttctggc tcccctcctg gccctccttg agtgccacc       1666 cataaatgcg aaatgccgtc agcagacaac ggttcccacc cctggggtcc tcacaacagg      1726
ctgcatcagg gctctcgacg cttgctggct tcatccatca actgctgggt gatctcctcg      1786
aacgcatcct tgatcgcgag ttcctcgaaa tcagcggcag cttgctccca gtggatccgt      1846
```

-continued

```
tccagctccg gcagcgccgc ccacagcgcc atgcgcaagt aggttccacg tgatcgctta   1906
gtgcgctcgg cgagcgcgtc caggcgctcg atcagctccg gttccaggcg cacggagacc   1966
acggggccgc gtccggcggg gttcttctgg ttggtggcca tgagaaattt cctctcgctt   2026
cggtagttgt aaacaatgtt tacaccgtgt cggggagagg ggtttttatt tttctcccgg   2086
gcactttcga gacgggtcat gccgtaagcg aggcgcgtgg ccacaccgca ctcggcgacg   2146
caggtgtcac ttgctccccg actgtcggcc gggaaggggg cgcgcagagc gtccaggagc   2206
gccgtagagc gcctgggacg gttcgtgtgg ggacttggtc gccccacggg gctttaatcg   2266
cttaaaaacg cgcacagcgc atttcttgcc acgggctagc gcgtgaccgc tgcgcgctca   2326
cttgctcagg aagaaaatca ttcctcgcct aaagcgcttc gcgcgctcgc cctctccgag   2386
ggggaaaact aaccacacac ctcatgcact aaagtgctga tttgcaggtc agcgcgtttt   2446
agcgtgcaaa aatagtgcgg aaaacggcga aaatggggc gcgacaatcc cctcagtggc   2506
tccccaaaat tcacctattc acatctgcta ctggctgact tctttcccga caaggggccc   2566
tgtgagggcg caggttgagc cacttttacg tcccggagat ccctttaggg cgtattcgag   2626
gtgtgctcag tgacccgctt cggcggggtg ggagtagcca aaagtccgac atttttaacg   2686
aacgttcgtt aaaatggggg catgactcag ggacctttga cctcagaaac cggcgcaatc   2746
ctgaatgatc ttggcgcagc agaccctctc gatgtggctg tccgggcacg ggagagtgcg   2806
catgttctct ctcaagtcgt ggagttttta gagcagatcg gccggtctgg ggatagcgat   2866
ttagacgcgg tgtatgagcg tgattggcag ctcgatgcag acacgttgac cttcattgcc   2926
caggcgttgg aggggttggc ggaccaggcc gaggcgaagg atgccgtgaa cgaatgacgg   2986
atatgtgtgc ccaatgcggt ggggaaatcc cgccccggcc tgaccccgc ggacgcaggg   3046
cgaagtattg ctcggatgct tgtcgggcgg cagcgagccg cgaacgcgcg cgccagcgcc   3106
acgcccagga ggtcgaagcc gcgcgtctcc aggccgcact cgatctgaaa accccgcagg   3166
agaccctggc agaggtagtc caggagcttc aggccaccac ccggattatc cgtgatcgag   3226
gggacgtgcc agcgtcgctg cgtccgctgg ttaatgctgc atccgaactg gtcaacgcag   3286
cgcaaccggt tgaggaatct aagtcattcc ccaaccggcg agtgcgtcgt gcagttaaac   3346
gaaagtttgc gataagcggg tgatgtaact gatggagatt tttacctggg ggtgtctcca   3406
gcgaggtggc caagtccgat tgtgttgagg attaccccaa acgtgcgggg attattcaaa   3466
atccactgtc caaccgcttt tccggttacc ccgcctccga tgcagcctac gagaatagag   3526
cccatgacca ttgcattgtg gctatatccc gcatttggat ccagcgccga gaaactggtg   3586
taggcaccag cagcgcagcc tgcaatgcga gcgccaatga taaccagggg gagggcgcga   3646
ggcattactc gattttcatc tgtggtctgt cgctgaatcg aagcagtgat ggcttcttca   3706
aatgcttcag ggtttgacgt ggggtccgag actgttgacg cagcttcctg cactgccttg   3766
atgaggacat cttcagggat ggaatcattg aacattcctc ccagctcaga gtggtttga   3826
acgttagccg aagggacatg cacatcgggg gaagcctggg cggctggagc aattaaagac   3886
agcgacagtg aagcaacgag agccgttaca gtggcacgag ttttttaaata catgaggcga   3946
acttaacaaa ccattgatag gttgtcgtgc ggtaaagata agaaaaggat aaagatatga   4006
aaacgttatt tatgaatctc ttaggtccgg cgcttgtagg agcggtaatc atggtcttga   4066
catggttatt tattgatttt gatgcacctg gagcatggct cggattcttt attatcacca   4126
ccatcagtga ttgctgcttt agaagtcatc cacggacttt gggaaaaacg gcagggatct   4186
tccactgaca atgattgata aaacctggtt gaacggaata caaaacgcgc aaaataacca   4246
```

```
ggcagttaaa agaaaaacca gataagctgc accaatactt gaaaaatgtt gaacgccccg    4306
acagctgtaa ctgtcgaggc gtcggctaac ccccagtcat cagctgggag aaagcactca    4366
aaa                                                                  4369
```

<210> SEQ ID NO 10
<211> LENGTH: 492
<212> TYPE: PRT
<213> ORGANISM: Corynebacterium thermoaminogenes

<400> SEQUENCE: 10

```
Met Thr Leu Ala Asp Ser Pro Gly Thr Tyr Thr Ala Asp Ala Trp Asn
1               5                   10                  15

Tyr Ser Thr Asp Leu Phe Asp Thr His Pro Glu Leu Ala Leu Arg Ser
            20                  25                  30

Arg Gly Trp Asn His Gln Asp Ala Ala Glu Phe Leu Ala His Leu Asp
        35                  40                  45

Arg Ser Met Phe His Gly Cys Pro Thr Arg Asp Phe Ser Ala Ala Trp
    50                  55                  60

Val Lys Asp Pro Glu Thr Gly Glu Thr Arg Pro Lys Leu His Arg Val
65                  70                  75                  80

Gly Thr Arg Ser Leu Ser Arg Cys Gln Tyr Val Ala Leu Thr His Pro
                85                  90                  95

Gln Arg Ser Ala Val Leu Val Leu Asp Ile Asp Ile Pro Ser His Gln
            100                 105                 110

Ala Gly Gly Asn Ile Glu His Leu His Pro Gln Val Tyr Ala Thr Leu
        115                 120                 125

Glu Arg Trp Ala Arg Val Glu Lys Ala Pro Ala Trp Ile Gly Val Asn
    130                 135                 140

Pro Leu Ser Gly Lys Cys Gln Leu Ile Trp Cys Ile Asp Pro Val Phe
145                 150                 155                 160

Ala Ala Glu Gly Thr Thr Ser Ser Asn Thr Arg Leu Leu Ala Ala Thr
                165                 170                 175

Thr Glu Glu Met Thr Arg Val Phe Gly Ala Asp Gln Ala Phe Ser His
            180                 185                 190

Arg Leu Ser Arg Trp Pro Leu His Val Phe Asp Asp Pro Thr Ala Tyr
        195                 200                 205

Ser Trp His Cys Gln His Asn Arg Val Asp Ile Leu Asp Glu Leu Met
    210                 215                 220

Glu Val Ala Arg Thr Met Thr Gly Ser Lys Lys Pro Arg Lys His Ala
225                 230                 235                 240

His Gln Glu Phe Ser Ser Gly Arg Ala Arg Ile Glu Ala Ala Arg Lys
                245                 250                 255

Ala Thr Ala Glu Ala Lys Ala Leu Ala Ala Leu Asp Ala Thr Leu Pro
            260                 265                 270

Thr Ala Leu Glu Ala Ser Gly Asp Leu Ile Asp Gly Val Arg Val Leu
        275                 280                 285

Trp Ala Ala Glu Gly Arg Ala Ala Arg Asp Glu Thr Ala Phe Arg His
    290                 295                 300

Ala Leu Thr Val Gly Tyr Gln Leu Lys Ala Ala Gly Glu Arg Leu Lys
305                 310                 315                 320

Asp Ala Lys Ile Ile Asp Ala Tyr Glu Arg Ala Tyr Asn Val Ala Gln
                325                 330                 335

Ala Val Gly Ala Asp Gly Arg Glu Pro Asp Leu Pro Ala Met Arg Asp
```

-continued

```
                        340                 345                 350
Arg Gln Thr Met Ala Arg Val Arg Ala Tyr Val Ala Lys Gly Gln
                355                 360                 365
Pro Thr Val Ser Ala Arg Ser Thr Gln Thr Gln Ser Ser Arg Gly Arg
            370                 375                 380
Lys Ala Leu Ala Thr Met Gly Arg Arg Gly Gly Gln Lys Ala Ala Glu
385                 390                 395                 400
Arg Trp Lys Thr Asp Pro Asn Gly Lys Tyr Ala Gln Glu Asn Arg Gln
                405                 410                 415
Arg Leu Glu Ala Ala Asn Lys Arg Arg Gln Val Ser Trp Asn Lys Tyr
            420                 425                 430
Ala Ser Thr Asn Ser Gly Tyr Gly Phe Arg His Val Trp Ala Ser Leu
        435                 440                 445
Glu Lys Cys Leu Arg Asp Glu Gln Ile Met Glu Glu Thr Gly Leu Ser
    450                 455                 460
Arg Ala Thr Val Thr Arg His Trp Val His Cys Glu Arg Leu Ala Cys
465                 470                 475                 480
Cys Gln Ile Leu Arg Gly Ala His Ala Val His Arg
                485                 490

<210> SEQ ID NO 11
<211> LENGTH: 22
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
aaccaggggg agggcgcgag gc                                          22

<210> SEQ ID NO 12
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 12
tctcgtaggc tgcatccgag gcgggg                                      26

<210> SEQ ID NO 13
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 13
gctctagagc aaccaggggg agggcgcgag gc                               32

<210> SEQ ID NO 14
<211> LENGTH: 36
<212> TYPE: DNA
<213> ORGANISM: ARTIFICIAL SEQUENCE
<220> FEATURE:
<223> OTHER INFORMATION: SYNTHETIC DNA

<400> SEQUENCE: 14
gctctagagc tctcgtaggc tgcatcggag gcgggg                           36

<210> SEQ ID NO 15
```

```
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 15
gctctagagc aaccaggggg agggcgcgag gc                                     32

<210> SEQ ID NO 16
<211> LENGTH: 36
<212> TYPE: DNA
<213> ORGANISM: ARTIFICIAL SEQUENCE
<220> FEATURE:
<223> OTHER INFORMATION: SYNTHETIC DNA

<400> SEQUENCE: 16
gctctagagc tctcgtaggc tgcatcggag gcgggg                                 36

<210> SEQ ID NO 17
<211> LENGTH: 32
<212> TYPE: DNA
<213> ORGANISM: ARTIFICIAL SEQUENCE
<220> FEATURE:
<223> OTHER INFORMATION: SYNTHETIC DNA

<400> SEQUENCE: 17
cccgttaact gcttgaaacc caggacaata ac                                     32

<210> SEQ ID NO 18
<211> LENGTH: 30
<212> TYPE: DNA
<213> ORGANISM: ARTIFICIAL SEQUENCE
<220> FEATURE:
<223> OTHER INFORMATION: SYNTHETIC DNA

<400> SEQUENCE: 18
cccgttaaca tgtacttcag aaaagattag                                        30

<210> SEQ ID NO 19
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 19
gatatctacg tgccgatcaa cgtctc                                            26

<210> SEQ ID NO 20
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 20
aggccttttt ttaaggcagt tattg                                             25
```